United States Patent
Hide et al.

(10) Patent No.: US 9,709,576 B2
(45) Date of Patent: *Jul. 18, 2017

(54) HISTAMINE RELEASER CONTAINED IN HUMAN SWEAT

(71) Applicant: Hiroshima University, Higashihiroshima-shi, Hiroshima (JP)

(72) Inventors: Michihiro Hide, Hiroshima (JP); Takaaki Hiragun, Hiroshima (JP); Kaori Ishii, Hiroshima (JP); Shoji Mihara, Hiroshima (JP); Makiko Hiragun, Hiroshima (JP); Jens-M Schroeder, Kiel (DE)

(73) Assignee: Hiroshima University, Hiroshima (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/248,106

(22) Filed: Aug. 26, 2016

(65) Prior Publication Data

US 2016/0363598 A1 Dec. 15, 2016

Related U.S. Application Data

(62) Division of application No. 14/409,730, filed as application No. PCT/JP2013/067396 on Jun. 25, 2013, now Pat. No. 9,457,071.

(30) Foreign Application Priority Data

Jun. 28, 2012 (JP) ................. 2012-145814

(51) Int. Cl.
| | |
|---|---|
| *A61K 39/02* | (2006.01) |
| *C07K 16/14* | (2006.01) |
| *G01N 33/68* | (2006.01) |
| *C07K 14/375* | (2006.01) |
| *A61K 39/00* | (2006.01) |
| *G01N 33/569* | (2006.01) |
| *A61K 38/00* | (2006.01) |

(52) U.S. Cl.
CPC ..... *G01N 33/6854* (2013.01); *A61K 39/0002* (2013.01); *C07K 14/375* (2013.01); *C07K 16/14* (2013.01); *G01N 33/56961* (2013.01); *A61K 38/00* (2013.01); *A61K 2039/577* (2013.01); *C07K 2317/76* (2013.01); *C07K 2319/30* (2013.01); *G01N 2333/37* (2013.01); *G01N 2800/20* (2013.01); *G01N 2800/202* (2013.01); *G01N 2800/24* (2013.01)

(58) Field of Classification Search
None
See application file for complete search history.

(56) References Cited

U.S. PATENT DOCUMENTS

2006/0088926 A1 4/2006 Ozawa et al.
2006/0134706 A1 6/2006 Hide et al.
2010/0311604 A1 12/2010 Takkinen et al.
2011/0117103 A1 5/2011 Hide et al.
2015/0212097 A1 7/2015 Hide et al.

FOREIGN PATENT DOCUMENTS

| EP | 0955366 A1 | 11/1999 |
|---|---|---|
| EP | 1607107 A1 | 12/2005 |
| EP | 1655307 A1 | 5/2006 |
| EP | 2292659 A1 | 3/2011 |
| JP | 3642340 A | 4/2005 |
| JP | 2008-069118 A | 3/2008 |
| JP | 2010-516747 A | 5/2010 |
| WO | 03/084991 A1 | 10/2003 |
| WO | 2005/005474 A1 | 1/2005 |
| WO | 2008/092993 A1 | 8/2008 |
| WO | 2009/133951 A1 | 11/2009 |

OTHER PUBLICATIONS

Rudikoff et al., "Single amino acid substitution altering antigen-binding specificity," Proceedings of the National Academy of Sciences of the United States of America (PNAS), 79: 1979-1983 (1982).
Skolnick et al., "From genes to protein structure and function: novel applications of computational approaches in the genomic era," TIBTECH, 18: 34-39 (2000).
Colman, "Effects of amino acid sequence changes on antibody-antigen interactions," Research in Immunology, 145: 33-36 (1994).
Lazar et al., "Transforming Growth Factor alpha: Mutation of Aspartic Acid 47 and Leucine 48 Results in Different Biological Activities," Molecular and Cellular Biology, 8: 1247-1252 (1988).
Office Action issued in related U.S. Appl. No. 14/421,821 dated Dec. 16, 2016.
Extended European Search Report issued in corresponding European Patent Application No. 13809354.7 dated Feb. 10, 2016.
Valenta et al., "Autoallergy: A pathogenetic factor in atopic dermatitis?" Journal of Allergy and Clinical Immunology, 105: 432-437 (2000).
Vilhelmsson, "Structural and functional studies of malassezia sympodialis-derived allergens," Department of Medicine Solna, Clinical Allergy Research Unit, Karolinska Institutet, XP55234699 (2008).
Partial Supplementary European Search Report issued in related European Patent Application No. 13879589.3 dated Apr. 20, 2016.
Ishii et al., "A human monoclonal IgE antibody that binds to MGL_1304, a major allergen in human sweat, without activation of mast cells and basophils," Biochemical and Biophysical Research Communications, 468: 99-104 (2015).

(Continued)

*Primary Examiner* — Jennifer Graser
(74) *Attorney, Agent, or Firm* — Morgan, Lewis & Bockius LLP

(57) ABSTRACT

Provided are a sweat allergy antigen, an antibody capable of binding to the antigen specifically, and others, which are produced utilizing a microorganism-originated protein that exists in sweat allergy patient in a dissolved state or a partial peptide of the protein.

12 Claims, 11 Drawing Sheets

(56) References Cited

OTHER PUBLICATIONS

"Product Catalog 2010 Bioporto Diagnostics," XP055257898, http://www.ngal.cz/files/bioporto-katalog-2010-en.pdf (2010).

Xu et al., "Malassezia globosa CBS 7966 hypothetical protein MGL_1304 partial mRNA," Database DDBJ/EMBL/GenBank [online], XM_001731984.1 (2008).

Rasool et al., "Cloning, characterization and expression of complete coding sequences of three IgE binding Malassezia furfur allergens, Mal f 7, Mal f 8 and Mal f 9.," European Journal of Biochemistry, 267: 4355-4361 (2000).

Lindberg et al., "Malassezia furfur mRNA coding for potential allergen, strain ATCC No. 42132," Database DDBJ/EMBL/GenBank [online], AJ011958.1 (2000).

Lindberg et al., "Malassezia sympodialis mRNA for allergen Mal s 8, strain ATCC No. 42132," Database DDBJ/EMBL/GenBank [online], AJ011958.2 (2002).

Kanbe et al., "Atopic *Dermatitis* and *Malassezia* Species: A Study of Antigenic Components of *Malassezia* Species for Immunoglobulin E of Patients with Atopic *Dermatitis*," Japanese Journal of Medical Mycology, 44: 71-75 (2003) see English abstract.

Shindo et al., "Histamine release- neutralization assay for sera of patients with atopic dermatitis and/or cholinergic urticaria is useful to screen type I hypersensitivity against sweat antigens," Archives of Dermatological Research, 304: 647-654 (2012).

Hiragun et al., "Fungal protein MGL_1304 in sweat is an allergen for atopic dermatitis patients," Journal of Allergy and Clinical Immunology, (2013).

International Search Report issued in corresponding International Patent Application No. PCT/JP2013/067396 dated Jul. 23, 2013.

Steinberger et al., "Construction of a Combinatorial IgE Library from an Allergic Patient," The Journal of Biological Chemistry, 271: 10967-10972 (1996).

Tanaka et al., "Cholinergic Urticaria Successfully Treated by Immunotherapy with Partially Purified Sweat Antigen," Allergy, 56: 54-57 (2007) (see English abstract on p. 57).

Tanaka et al., "Semi-purification of the immunoglobulin E-sweat antigen acting on mast cells and basophils in atopic dermatitis," Experimental Dermatology, 15: 283-290 (2006).

Fairley et al., "A Pathogenic Role for IgE in Autoimmunity: Bullous Pemphigoid IgE Reproduces the Early Phase of Lesion Development in Human Skin Grafted to nu/nu Mice," Journal of Investigative Dermatology, 127: 2605-2611 (2007).

Human IgE (non-Immune), BIOPORTO Diagnostics (2011).

International Preliminary Report on Patentability issued in related International Patent Application No. PCT/JP2013/071715 dated Feb. 26, 2015.

International Preliminary Report on Patentability issued in corresponding International Patent Application No. PCT/JP2013/067396 dated Dec. 28, 2014.

International Search Report issued in related International Patent Application No. PCT/JP2013/071715 dated Nov. 12, 2013.

Xu et al., "hypothetical protein MGL_1304 [Malassezia globosa CBS 7966]," RefSeq. [online], XP_001732036.1 (2008).

Smith-2

SEQUENCE LISTING

<160> NUMBER OF SEQ ID NOS: 13

<210> SEQ ID NO 1
<211> LENGTH: 183
<212> TYPE: PRT
<213> ORGANISM: Malassezia globosa

<400> SEQUENCE: 1

Met Val Ser Leu Asn Ile Phe Ser Ala Ala Phe Val Ala Ser Leu Ala
1               5                   10                  15

Ser Ala Val Phe Ala Ala Pro Ser Ala Leu Glu Arg Arg Ala Ala Pro
                20                  25                  30

Asp Asn Thr Val Trp Val Thr Ser Val Ala Asp His Cys Leu Ile Leu
            35                  40                  45

Pro Arg His Lys Met Ser Val Gly Asp Ser Glu Ser Pro Gly Asn Met
        50                  55                  60

Arg Ser Phe Cys Thr Lys Pro Tyr Ser Ser Lys Gln Gly Gln Leu Ala
65                  70                  75                  80

Ser Asp Phe Trp Thr Lys Ala His Phe Lys Lys Thr Asp Lys Tyr Val
                85                  90                  95

Gln Ile Thr Gly Cys Ile Asn Pro Asn Val Gln Ser Thr Leu Leu Ser
            100                 105                 110

Asn Asp Glu Gly Gly Gln Tyr Asp Ser Asn Gly Gly Gly Gly Gly Arg
        115                 120                 125

Gly Asn Pro Ala Gly Ser Val Cys Leu Gly Tyr Ser Ser Tyr Val Glu
    130                 135                 140

Leu Val Glu Pro Ala Gly Asn Arg Ala Cys Ile Arg Cys Cys Tyr Asp
145                 150                 155                 160

Pro Ser Asp Cys Asp Val Ser Gln Asp Glu Ala Gly Cys Glu Thr Val
                165                 170                 175

Ile Pro Gly Lys Tyr Asp Cys
            180

<210> SEQ ID NO 2
<211> LENGTH: 142
<212> TYPE: PRT
<213> ORGANISM: Malassezia globosa

<400> SEQUENCE: 2

Pro Asp Asn Thr Val Trp Val Thr Ser Val Ala Asp His Cys Leu Ile
1               5                   10                  15

Leu Pro Arg His Lys Met Ser Val Gly Asp Ser Glu Ser Pro Gly Asn
                20                  25                  30

Met Arg Ser Phe Cys Thr Lys Pro Tyr Ser Ser Lys Gln Gly Gln Leu
            35                  40                  45

Ala Ser Asp Phe Trp Thr Lys Ala His Phe Lys Lys Thr Asp Lys Tyr
        50                  55                  60

Val Gln Ile Thr Gly Cys Ile Asn Pro Asn Val Gln Ser Thr Leu Leu
65                  70                  75                  80

Ser Asn Asp Glu Gly Gly Gln Tyr Asp Ser Asn Gly Gly Glu Gly Gly
                85                  90                  95

Arg Gly Asn Pro Ala Gly Ser Val Cys Leu Gly Tyr Ser Ser Tyr Val
            100                 105                 110

Glu Leu Val Glu Pro Ala Gly Asn Arg Ala Cys Ile Arg Cys Cys Tyr
        115                 120                 125

Asp Pro Ser Asp Cys Asp Val Ser Gln Asp Glu Ala Gly Cys

```
                130                 135                 140

<210> SEQ ID NO 3
<211> LENGTH: 152
<212> TYPE: PRT
<213> ORGANISM: Malassezia globosa

<400> SEQUENCE: 3

Pro Asp Asn Thr Val Trp Val Thr Ser Val Ala Asp His Cys Leu Ile
1               5                   10                  15

Leu Pro Arg His Lys Met Ser Val Gly Asp Ser Glu Ser Pro Gly Asn
            20                  25                  30

Met Arg Ser Phe Cys Thr Lys Pro Tyr Ser Ser Lys Gln Gly Gln Leu
        35                  40                  45

Ala Ser Asp Phe Trp Thr Lys Ala His Phe Lys Lys Thr Asp Lys Tyr
50                  55                  60

Val Gln Ile Thr Gly Cys Ile Asn Pro Asn Val Gln Ser Thr Leu Leu
65                  70                  75                  80

Ser Asn Asp Glu Gly Gly Gln Tyr Asp Ser Asn Gly Gly Glu Gly Gly
                85                  90                  95

Arg Gly Asn Pro Ala Gly Ser Val Cys Leu Gly Tyr Ser Ser Tyr Val
            100                 105                 110

Glu Leu Val Glu Pro Ala Gly Asn Arg Ala Cys Ile Arg Cys Cys Tyr
        115                 120                 125

Asp Pro Ser Asp Cys Asp Val Ser Gln Asp Glu Ala Gly Cys Glu Thr
130                 135                 140

Val Ile Pro Gly Lys Tyr Asp Cys
145                 150

<210> SEQ ID NO 4
<211> LENGTH: 147
<212> TYPE: PRT
<213> ORGANISM: Malassezia globosa

<400> SEQUENCE: 4

Glu Arg Arg Ala Ala Pro Asp Asn Thr Val Trp Val Thr Ser Val Ala
1               5                   10                  15

Asp His Cys Leu Ile Leu Pro Arg His Lys Met Ser Val Gly Asp Ser
            20                  25                  30

Glu Ser Pro Gly Asn Met Arg Ser Phe Cys Thr Lys Pro Tyr Ser Ser
        35                  40                  45

Lys Gln Gly Gln Leu Ala Ser Asp Phe Trp Thr Lys Ala His Phe Lys
50                  55                  60

Lys Thr Asp Lys Tyr Val Gln Ile Thr Gly Cys Ile Asn Pro Asn Val
65                  70                  75                  80

Gln Ser Thr Leu Leu Ser Asn Asp Glu Gly Gly Gln Tyr Asp Ser Asn
                85                  90                  95

Gly Gly Glu Gly Gly Arg Gly Asn Pro Ala Gly Ser Val Cys Leu Gly
            100                 105                 110

Tyr Ser Ser Tyr Val Glu Leu Val Glu Pro Ala Gly Asn Arg Ala Cys
        115                 120                 125

Ile Arg Cys Cys Tyr Asp Pro Ser Asp Cys Asp Val Ser Gln Asp Glu
        130                 135                 140

Ala Gly Cys
145
```

```
<210> SEQ ID NO 5
<211> LENGTH: 157
<212> TYPE: PRT
<213> ORGANISM: Malassezia globosa

<400> SEQUENCE: 5

Glu Arg Arg Ala Ala Pro Asp Asn Thr Val Trp Val Thr Ser Val Ala
1               5                   10                  15

Asp His Cys Leu Ile Leu Pro Arg His Lys Met Ser Val Gly Asp Ser
            20                  25                  30

Glu Ser Pro Gly Asn Met Arg Ser Phe Cys Thr Lys Pro Tyr Ser Ser
        35                  40                  45

Lys Gln Gly Gln Leu Ala Ser Asp Phe Trp Thr Lys Ala His Phe Lys
    50                  55                  60

Lys Thr Asp Lys Tyr Val Gln Ile Thr Gly Cys Ile Asn Pro Asn Val
65                  70                  75                  80

Gln Ser Thr Leu Leu Ser Asn Asp Glu Gly Gln Tyr Asp Ser Asn
                85                  90                  95

Gly Gly Glu Gly Gly Arg Gly Asn Pro Ala Gly Ser Val Cys Leu Gly
            100                 105                 110

Tyr Ser Tyr Val Glu Leu Val Glu Pro Ala Gly Asn Arg Ala Cys
        115                 120                 125

Ile Arg Cys Cys Tyr Asp Pro Ser Asp Cys Asp Val Ser Gln Asp Glu
130                 135                 140

Ala Gly Cys Glu Thr Val Ile Pro Gly Lys Tyr Asp Cys
145                 150                 155

<210> SEQ ID NO 6
<211> LENGTH: 152
<212> TYPE: PRT
<213> ORGANISM: Malassezia globosa

<400> SEQUENCE: 6

Ala Pro Ser Ala Leu Glu Arg Arg Ala Ala Pro Asp Asn Thr Val Trp
1               5                   10                  15

Val Thr Ser Val Ala Asp His Cys Leu Ile Leu Pro Arg His Lys Met
            20                  25                  30

Ser Val Gly Asp Ser Glu Ser Pro Gly Asn Met Arg Ser Phe Cys Thr
        35                  40                  45

Lys Pro Tyr Ser Ser Lys Gln Gly Gln Leu Ala Ser Asp Phe Trp Thr
    50                  55                  60

Lys Ala His Phe Lys Lys Thr Asp Lys Tyr Val Gln Ile Thr Gly Cys
65                  70                  75                  80

Ile Asn Pro Asn Val Gln Ser Thr Leu Leu Ser Asn Asp Glu Gly Gly
                85                  90                  95

Gln Tyr Asp Ser Asn Gly Gly Glu Gly Gly Arg Gly Asn Pro Ala Gly
            100                 105                 110

Ser Val Cys Leu Gly Tyr Ser Tyr Val Glu Leu Val Glu Pro Ala
        115                 120                 125

Gly Asn Arg Ala Cys Ile Arg Cys Cys Tyr Asp Pro Ser Asp Cys Asp
130                 135                 140

Val Ser Gln Asp Glu Ala Gly Cys
145                 150

<210> SEQ ID NO 7
<211> LENGTH: 162
<212> TYPE: PRT
```

<213> ORGANISM: Artificial
<220> FEATURE:
<223> OTHER INFORMATION: Peptide fragment 22-183 of MGL_1304

<400> SEQUENCE: 7

Ala Pro Ser Ala Leu Glu Arg Arg Ala Ala Pro Asp Asn Thr Val Trp
1               5                   10                  15

Val Thr Ser Val Ala Asp His Cys Leu Ile Leu Pro Arg His Lys Met
                20                  25                  30

Ser Val Gly Asp Ser Glu Ser Pro Gly Asn Met Arg Ser Phe Cys Thr
            35                  40                  45

Lys Pro Tyr Ser Ser Lys Gln Gly Gln Leu Ala Ser Asp Phe Trp Thr
        50                  55                  60

Lys Ala His Phe Lys Lys Thr Asp Lys Tyr Val Gln Ile Thr Gly Cys
65                  70                  75                  80

Ile Asn Pro Asn Val Gln Ser Thr Leu Leu Ser Asn Asp Glu Gly Gly
                85                  90                  95

Gln Tyr Asp Ser Asn Gly Gly Glu Gly Gly Arg Gly Asn Pro Ala Gly
            100                 105                 110

Ser Val Cys Leu Gly Tyr Ser Ser Tyr Val Glu Leu Val Glu Pro Ala
        115                 120                 125

Gly Asn Arg Ala Cys Ile Arg Cys Cys Tyr Asp Pro Ser Asp Cys Asp
    130                 135                 140

Val Ser Gln Asp Glu Ala Gly Cys Glu Thr Val Ile Pro Gly Lys Tyr
145                 150                 155                 160

Asp Cys

<210> SEQ ID NO 8
<211> LENGTH: 34
<212> TYPE: DNA
<213> ORGANISM: Artificial
<220> FEATURE:
<223> OTHER INFORMATION: PCR primer

<400> SEQUENCE: 8
ggggtaccgt atccctcaac attttctcag ctgc                         34

<210> SEQ ID NO 9
<211> LENGTH: 34
<212> TYPE: DNA
<213> ORGANISM: Artificial
<220> FEATURE:
<223> OTHER INFORMATION: PCR primer

<400> SEQUENCE: 9
cccaagcttt tagcagtcgt acttgccggg gatg                         34

<210> SEQ ID NO 10
<211> LENGTH: 50
<212> TYPE: PRT
<213> ORGANISM: Malassezia globosa

<400> SEQUENCE: 10

Met Val Ser Leu Asn Ile Phe Ser Ala Ala Phe Val Ala Ser Leu Ala
1               5                   10                  15

Ser Ala Val Phe Ala Ala Pro Ser Ala Leu Glu Arg Arg Ala Ala Pro
                20                  25                  30

Asp Asn Thr Val Trp Val Thr Ser Val Ala Asp His Cys Leu Ile Leu
            35                  40                  45

```
Pro Arg
    50

<210> SEQ ID NO 11
<211> LENGTH: 55
<212> TYPE: PRT
<213> ORGANISM: Malassezia globosa

<400> SEQUENCE: 11

Leu Ile Leu Pro Arg His Lys Met Ser Val Gly Asp Ser Glu Ser Pro
1               5                   10                  15

Gly Asn Met Arg Ser Phe Cys Thr Lys Pro Tyr Ser Ser Lys Gln Gly
            20                  25                  30

Gln Leu Ala Ser Asp Phe Trp Thr Lys Ala His Phe Lys Lys Thr Asp
        35                  40                  45

Lys Tyr Val Gln Ile Thr Gly
    50                  55

<210> SEQ ID NO 12
<211> LENGTH: 45
<212> TYPE: PRT
<213> ORGANISM: Malassezia globosa

<400> SEQUENCE: 12

Val Gln Ile Thr Gly Cys Ile Asn Pro Asn Val Gln Ser Thr Leu Leu
1               5                   10                  15

Ser Asn Asp Glu Gly Gly Gln Tyr Asp Ser Asn Gly Gly Glu Gly Gly
            20                  25                  30

Arg Gly Asn Pro Ala Gly Ser Val Cys Leu Gly Tyr Ser
        35                  40                  45

<210> SEQ ID NO 13
<211> LENGTH: 43
<212> TYPE: PRT
<213> ORGANISM: Malassezia globosa

<400> SEQUENCE: 13

Ser Tyr Val Glu Leu Val Glu Pro Ala Gly Asn Arg Ala Cys Ile Arg
1               5                   10                  15

Cys Cys Tyr Asp Pro Ser Asp Cys Asp Val Ser Gln Asp Glu Ala Gly
            20                  25                  30

Cys Glu Thr Val Ile Pro Gly Lys Tyr Asp Cys
        35                  40
```

HISTAMINE RELEASER CONTAINED IN HUMAN SWEAT

A computer readable text file, entitled "SequenceListing.txt," created on or about Mar. 10, 2015 with a file size of about 15 kb contains the sequence listing for this application and is hereby incorporated by reference in its entirety.

TECHNICAL FIELD

This application claims priority to Japanese Patent Application No. 2012-145814, filed Jun. 28, 2012 and incorporated by reference herein in its entirety.

The present invention relates to clinical application of a novel histamine releaser contained in human sweat (such as measurement of antigen-specific antibody concentration in a patient serum, preparation of an antibody to a sweat antigen, and a specific hyposensitization therapy).

BACKGROUND ART

Most of atopic dermatitis patients exhibit an immediate-type allergic reaction to their own sweat and a roughly purified sweat antigen. A roughly purified sweat antigen and an antibody specifically binding thereto have been reported (Patent Document 1 and Patent Document 2). However, a real molecule (sweat antigen) thereof is unknown.

CITATION LIST

Patent Documents

Patent Document 1: WO 2005-005474
Patent Document 2: WO 2009-133951

SUMMARY OF THE INVENTION

The present inventors have purified a human sweat antigen from human sweat using a histamine release activity from peripheral blood basophils of atopic dermatitis patient as an index and have identified MGL_1304, which is a protein derived from *Malassezia globosa*, as the human sweat antigen by mass spectrometry.

In one aspect, the present invention provides a sweat allergy antigen protein that is a protein derived from a microorganism. For example, the present invention provides a protein consisting of an amino acid sequence represented by SEQ ID NO: 1.

In one aspect, the present invention provides an MGL_1304 partial peptide. For example, the present invention provides a peptide consisting of an amino acid sequence represented by any one of SEQ ID NOs: 2 to 7.

In one aspect, the present invention provides a gene encoding a sweat allergy antigen protein that is a protein derived from a microorganism and a gene encoding a MGL_1304 partial peptide.

In one aspect, the present invention provides an antibody or an antibody fragment specifically binding to a sweat allergy antigen protein that is a protein derived from a microorganism or a MGL_1304 partial peptide.

In one aspect, the present invention provides a composition or kit for detecting a sweat allergy antigen, or a composition or kit for measuring an amount of a sweat allergy antigen, comprising an antibody or an antibody fragment specifically binding to a sweat allergy antigen protein that is a protein derived from a microorganism or the MGL_1304 partial peptide.

In one aspect, the present invention provides a composition or kit for detecting an antibody binding to a sweat allergy antigen, or a composition or kit for measuring an amount of a antigen binding to a sweat allergy antigen, comprising a sweat allergy antigen protein that is a protein derived from a microorganism or a MGL_1304 partial peptide.

In one aspect, the present invention provides a composition or kit for diagnosing a sweat allergy or a disease related to a sweat allergy antigen, comprising:
(i) a sweat allergy antigen protein that is a protein derived from a microorganism or a MGL_1304 partial peptide; or
(ii) an antibody or an antibody fragment specifically binding to the sweat allergy antigen protein that is a protein derived from a microorganism or a MGL_1304 partial peptide.

In one aspect, the present invention provides a composition for treatment of a sweat allergy or a disease relating to a sweat allergy antigen comprising a sweat allergy antigen protein that is a protein derived from a microorganism or a MGL_1304 partial peptide.

In one aspect, the present invention provides a composition for removal or neutralization of a sweat allergy antigen or a material for removing a sweat allergy antigen comprising an antibody specifically binding to a sweat allergy antigen protein that is a protein derived from a microorganism or a MGL_1304 partial peptide.

In one aspect, the present invention provides a composition or kit for determining an effect of a hyposensitization therapy comprising a sweat allergy antigen protein that is a protein derived from a microorganism or a MGL_1304 partial peptide.

In one aspect, the present invention provides a method for manufacturing a sweat allergy antigen protein comprising a step of culturing *Malassezia globosa* at pH 7 to pH 9, and a step of purifying a sweat allergy antigen protein.

BRIEF DESCRIPTION OF DRAWINGS

A recombinant protein of MGL_1304 was produced by *E. coli*.

In FIG. 6, B shows a binding ability of the protein truncated at the N-terminal or the C-terminal of MGL_1304 to atopic dermatitis patient serum IgE. In FIGS. 6, C and D show histamine release activity of the protein truncated at the N-terminal or the C-terminal of MGL_1304. In FIG. 6, E shows binding of an MGL_1304 recombinant protein and a partial peptide thereof to a Smith2 antibody, and serums (AD1 and AD2) derived from two atopic dermatitis patients.

FIG. 8 shows that pretreatment of the serum with a fusion protein (rTF-MGL) of Trigger Factor and rMGL resulted in disappearance of the binding property of IgE to QRX and rMGL.

In FIG. 11, B shows correlation of histamine releasability between a partially purified sweat antigen (QR) and the MGL_1304 recombinant protein (rMGL_1304).

EMBODIMENT FOR CARRYING OUT THE INVENTION

1. Sweat Allergy Antigen Protein

Figure 1:
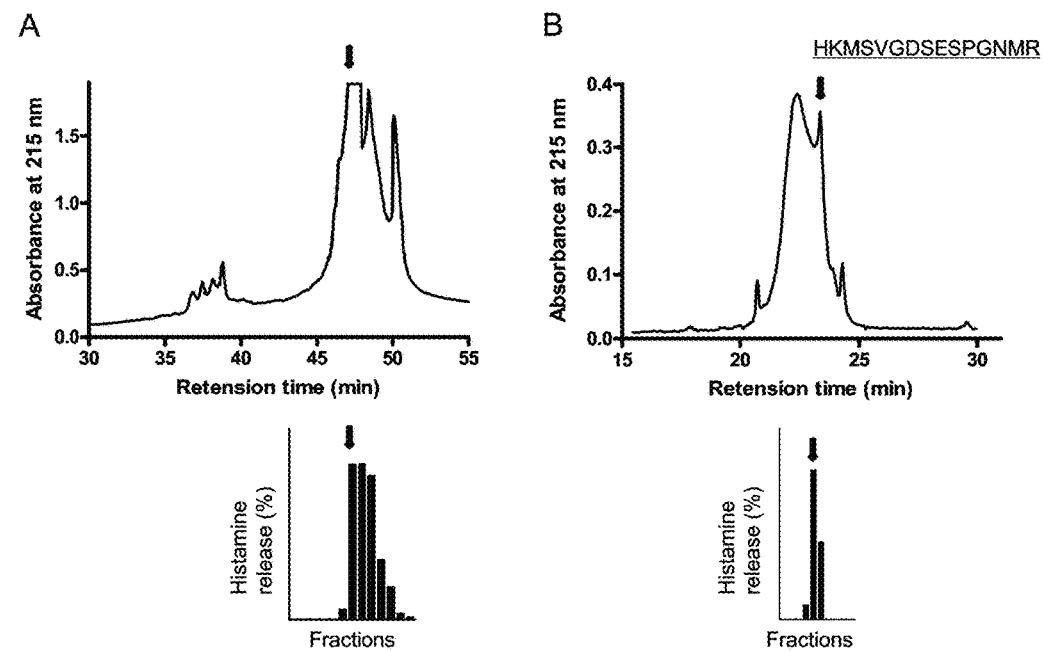
FIG. 1 shows that an amino acid sequence identical to MGL_1304 was detected by mass spectrometry after conducting further purification of partially purified sweat antigens (hereinafter also referred to as QRX).

In a first aspect, the present invention provides a sweat allergy antigen protein that is a protein derived from a microorganism.

As used herein, microorganisms may be *Malassezia globosa*, and *Malassezia globosa* may be *Malassezia globosa* (No. MYA-4612) purchasable from ATCC, for example. The protein derived from a microorganism may be a protein produced by *Malassezia globosa*. The protein produced by *Malassezia globosa* may be a protein secreted outside a fungus cell or may be a protein present in a fungus cell.

Examples of the proteins secreted outside the *Malassezia globosa* fungus cell include a protein coded by an MGL_1304 gene (e.g., a protein comprising an amino acid sequence represented by SEQ ID NO: 1) and a protein present in a culture supernatant of *Malassezia globosa* and binding to serum derived from a sweat allergy patient and/or smith2 antibodies (antibody produced by a hybridoma of Accession No. FERM BP-11111). The protein encoded by the MGL_1304 gene (e.g., a protein consisting of the amino acid sequence represented by SEQ ID NO: 1) may be a protein expressed in an appropriate host such as *E. coli*, COS7 cells and *Malassezia globosa*. The amino acid sequence represented by SEQ ID NO: 1 is as follows:

```
SEQ ID NO 1:
MVSLNIFSAAFVASLASAVFAAPSALERRAAPDNTVWVTSVADHCLILPR

HKMSVGDSESPGNMRSFCTKPYSSKQGQLASDFWTKAHFKKTDKYVQITG

CINPNVQSTLLSNDEGGQYDSNGGEGGRGNPAGSVCLGYSSYVELVEPAG

NRACIRCCYDPSDCDVSQDEAGCETVIPGKYDC.
```

Examples of a protein present in the *Malassezia globosa* fungus cell include a protein present in a fungus cell of *Malassezia globosa* and binding to serum derived from a sweat allergy patient and/or smith2 antibodies.

The protein present in a culture supernatant of *Malassezia globosa* and binding to serum derived from a sweat allergy patient and/or smith2 antibodies may be a protein having a molecular weight of about 17 kDa measured by SDS-PAGE. The protein present in a cell of *Malassezia globosa* and binding to serum derived from a sweat allergy patient and/or smith2 antibodies may be a protein having a molecular weight of about 30 kDa measured by SDS-PAGE. "About 17 kDa" and "about 30 kDa" described above are reasonably recognized by those skilled in the art as molecular weights measured by experiments (SDS-PAGE). For example, "about 17 kDa" and "about 30 kDa" described above may be molecular weights not exceeding ranges of "from 14 kDa to 20 kDa" and "from 27 kDa to 33 kDa", respectively. The protein present in a culture supernatant or a fungus cell of *Malassezia globosa* and binding to serum derived from a sweat allergy patient and/or smith2 antibodies may be a protein having histamine releasing activity for basophils derived from a sweat allergy patient and/or a protein which induces histamine release via IgE from a cell expressing an IgE receptor.

As used herein, a sweat allergy antigen is an antigenic substance (hereinafter also referred to as a sweat antigen) which is contained in human sweat and which induces an allergic reaction to cause diseases such as atopic dermatitis and cholinergic urticaria, and a sweat allergy antigen protein is a sweat allergy antigen that is a protein. In one embodiment, the sweat allergy antigen protein is dissolved in sweat.

As used herein, the sweat allergy antigen has histamine release activity. Histamine release activity can be determined in accordance with a known method (Koro, O. et al., J. Allergy Clin. Immunol., 103, 663-670, 1999). For example, histamine release activity may be determined by contacting a sweat allergy antigen and an IgE antibody with a cell expressing an IgE receptor on a cell surface and measuring an amount of histamine secreted from the cell. Examples of cells expressing IgE receptors on the cell surfaces include, basophils, mast cells (mastocytes) and a cell line artificially prepared by expressing IgE receptor gene which is able to release a chemical transmitter such as histamine.

For example, when an amount of histamine is measured and an amount of free histamine is within a range of from 3 to 97% relative to the total amount of histamine, it can be determined that the histamine release activity is positive (Koro, O. et al., J. Allergy Clin. Immunol., 103, 663-670, 1999).

"sweat allergy antigen protein that is a protein derived from microorganisms" provided by the present invention may be prepared by purification from a secretion of a sweat gland using the histamine release activity as an index. For example, the sweat allergy antigen protein is prepared by a method comprising a step of concentrating human sweat, a step of purification using anion-exchange column chromatography, a step of purification using reverse-phase column chromatography, and a step of purification using gel filtration column chromatography. Therefore, in one embodiment, the present invention provides a sweat allergy antigen protein that is a protein derived from a microorganism and that is prepared by a method comprising a step of concentrating human sweat, a step of purification using anion-exchange column chromatography, a step of purification using reverse-phase column chromatography, and a step of purification using gel filtration column chromatography. In one embodiment, the present invention provides a method of manufacturing a sweat allergy antigen protein that is a protein derived from a microorganism comprising a step of concentrating human sweat, a step of purification using anion-exchange column chromatography, a step of purification using reverse-phase column chromatography, and a step of purification using gel filtration column chromatography.

"sweat allergy antigen protein that is a protein derived from a microorganism" provided by the present invention may be prepared from a culture of *Malassezia globosa*. Condition and method for the culture may be appropriately selected by those skilled in the art and those are not limited.

For example, "sweat allergy antigen protein that is a protein derived from a microorganism" provided by the present invention may be prepared by culturing *Malassezia globosa* (No. MYA-4612) available from ATCC in a 2693 mDixon medium (2693 mDixon medium is prepared by mixing Malt Extract (36 g); Desiccated Oxbile (20 g); Tween 40 (10 ml); Peptone (6.0 g); Glycerol (2.0 ml); Oleic Acid (2.0 ml); and DI Water (1.0 L) to acquire a solution adjusted to pH 6 by using HC1 and autoclaving the solution put into a suitable container at 121° C.) at 32° C. for four days, centrifuging the culture (at 2000 rpm for 10 minutes), and purifying an acquired supernatant or lysate (cell lysate) of fungus cells dissolved in a phosphate buffer solution (PBS) using binding to the Smith2 antibody as an index.

Therefore, in one embodiment, the present invention provides a sweat allergy antigen protein that is a protein derived from a microorganism and that is prepared by a step of culturing *Malassezia globosa* and a step of purifying a culture supernatant or fungus cell lysate using binding to the Smith2 antibody as an index. In one embodiment, the present invention provides a method of manufacturing a sweat allergy antigen protein that is a protein derived from a microorganism comprising a step of culturing *Malassezia globosa* and a step of purifying a culture supernatant or fungus cell lysate using binding to the Smith2 antibody as an index.

The production of the MGL_1304 protein (protein encoded by the MGL_1304 gene), i.e., the sweat allergy antigen protein from *Malassezia globosa*, is increased when *Malassezia globosa* is cultured at pH 8 as compared to when *Malassezia globosa* is cultured at pH 4 or pH 6. Therefore, *Malassezia globosa* may be cultured at pH 7 to 10, preferably pH 7 to 9, more preferably pH 8.

The purification of the sweat allergy antigen protein from a culture solution of *Malassezia globosa* is performed as a more simple operation when the culture solution contains no protein other than the sweat allergy antigen protein. Therefore, after *Malassezia globosa* is cultured at pH 4 to 6, preferably pH 4 to increase a fungus cell amount, a culture supernatant is discarded and *Malassezia globosa* is subsequently cultured by using a buffer solution (e.g., PBS/HEPES/glucose buffer solution) of pH 7 to 10, preferably pH 7 to 9, more preferably pH 8, so as to produce a sweat allergy antigen protein, and the sweat allergy antigen protein may be purified from the buffer solution containing the obtained sweat allergy antigen protein. The purification may be performed by column chromatography (e.g., ion-exchange column chromatography, reverse-phase column chromatography, and gel filtration column chromatography).

The "sweat allergy antigen protein that is a protein derived from a microorganism" provided by the present invention may be prepared by expressing a protein encoded by the MGL_1304 gene (e.g., a protein comprising the amino acid sequence represented by SEQ ID NO: 1) in a suitable host such as a microorganism and a cell (e.g., *E. coli*, COS7 cells, and *Malassezia globosa*).

Therefore, in one embodiment, the present invention provides a sweat allergy antigen protein that is a protein derived from a microorganism and that is prepared by expressing a protein encoded by the MGL_1304 gene (e.g., a protein comprising the amino acid sequence represented by SEQ ID NO: 1) in a suitable host such as a microorganism and a cell (e.g., *E. coli*, COS7 cells, and *Malassezia globosa*). In one embodiment, the present invention provides a method of manufacturing a sweat allergy antigen protein that is a protein derived from a microorganism comprising a step of expressing a protein encoded by the MGL_1304 gene (e.g., a protein consisting of the amino acid sequence represented by SEQ ID NO: 1) in a suitable host such as a microorganism and a cell (e.g., *E. coli*, COS7 cells, and *Malassezia globosa*).

In one embodiment, the present invention provides an analog of the protein encoded by the MGL_1304 gene (e.g., a protein consisting of the amino acid sequence represented by SEQ ID NO: 1). The analog is not particularly limited as long as the analog can be prepared based on the protein encoded by the MGL_1304 gene or the protein consisting of the amino acid sequence represented by SEQ ID NO: 1. Examples of the analog of the protein consisting of the amino acid sequence represented by SEQ ID NO: 1 include a protein consisting of an amino acid sequence having 60, 70, 80, 90, or 95% or more identity to the amino acid sequence represented by SEQ ID NO: 1, and a protein consisting of an amino acid sequence with 1, 2, 3, 4, 5, 6, 7, 8, 9, 10, 11, 12, 13, 14, 15, 16, 17, 18, 19, or 20 amino acids deleted, substituted, or added in the amino acid sequence represented by SEQ ID NO: 1.

Another example of the analog of the protein encoded by the MGL_1304 gene (e.g., a protein consisting of the amino acid sequence represented by SEQ ID NO: 1) may be a protein encoded by the MGL_1304 gene (e.g., a protein consisting of the amino acid sequence represented by SEQ ID NO: 1) to which a tag is added. As used herein, a tag means a portion added to a protein or a polypeptide for purification, detection, etc. of the protein or polypeptide and is exemplified by histidine (His), glutathione-S-transferase (GST), a maltose-binding protein (MBP), myc, a FLAG tag, Trigger Factor (TF), etc. A polypeptide having a tag added thereto is obtained by expressing the polypeptide by using an expression vector, for example, pET30a (manufactured by Novagen) (for His tags), pGEX (manufactured by GE Healthcare Bio-Sciences Corp.) (for GST tags), and a pCold TF vector (manufactured by TAKARA BIO INC.), in a suitable host such as a microorganism and a cell (e.g., *E. coli*, COS7 cells, and *Malassezia globosa*).

The analog of the protein encoded by the MGL_1304 gene (e.g., a protein consisting of the amino acid sequence represented by SEQ ID NO: 1) is able to bind to the IgE antibody present in a serum of a sweat allergy patient.

The analog of the protein encoded by the MGL_1304 gene (e.g., a protein consisting of the amino acid sequence represented by SEQ ID NO: 1) may have the histamine release activity.

The protein encoded by the MGL_1304 gene (e.g., a protein consisting of the amino acid sequence represented by SEQ ID NO: 1) and the analog thereof provided by the preset invention can be manufactured by a conventional genetic engineering method or a method used in peptide synthesis. The manufactured proteins and the analogs thereof may be used as the sweat allergy antigen. Therefore, in one embodiment, the present invention provides a use of a protein derived from a microorganism or an analog thereof (e.g., a protein consisting of the amino acid sequence represented by SEQ ID NO: 1 and an analog thereof, and a protein present in a culture supernatant of *Malassezia globosa* and binding to serum derived from a sweat allergy patient and/or smith2 antibodies) in manufacturing of the sweat allergy antigen.

The protein or polypeptide provided by the present invention binds to the IgE antibody and/or the IgG antibody binding to a sweat allergy antigen present in a serum of a sweat allergy patient, and therefore can be used for detecting, quantifying, or removing IgE antibody and/or IgG antibody binding to the sweat allergy antigen present in a serum of a sweat allergy patient. Thus, in one embodiment, the present invention provides use of a protein derived from a microorganism (e.g., the proteins encoded by the MGL_1304 gene (e.g., a protein consisting of the amino acid sequence represented by SEQ ID NO: 1) and the analogs thereof) in detection, quantification, neutralization, or removal of IgE antibody and/or IgG antibody binding to a sweat allergy antigen.

The protein or polypeptide provided by the present invention may be an isolated protein or polypeptide.

2. MGL_1304 Partial Peptide

In a second aspect, the present invention provides an MGL_1304 partial peptide.

The MGL_1304 partial peptide may be a sweat allergy antigen. Therefore, in one embodiment, the present invention provides use of the MGL_1304 partial peptide in manufacturing of a sweat allergy antigen.

As used herein, the MGL_1304 partial peptide may be a peptide corresponding to a portion of a protein encoded by the MGL_1304 gene. The MGL_1304 partial peptide may be a peptide consisting of a portion of the amino acid sequence represented by SEQ ID NO: 1. Examples of the MGL_1304 partial peptide include a peptide corresponding to a residue 32-173 of the polypeptide represented by SEQ ID NO: 1 (SEQ ID NO: 2), a peptide corresponding to a residue 32-183 of the polypeptide represented by SEQ ID NO: 3), a peptide corresponding to a residue 27-173 of the polypeptide represented by SEQ ID NO: 1 (SEQ ID NO: 4), a peptide corresponding to a residue 27-183 of the polypeptide represented by SEQ ID NO: 1 (SEQ ID NO: 5), a peptide corresponding to a residue 22-173 of the polypeptide represented by SEQ ID NO: 1 (SEQ ID NO: 6) or a peptide corresponding to a residue 22-183 of the polypeptide represented by SEQ ID NO: 1 (SEQ ID NO: 7).

Therefore, in one embodiment, the present invention provides a peptide comprising an amino acid sequence represented by any of SEQ ID NOs: 2 to 7.

The MGL_1304 partial peptide may be a peptide binding to the IgE antibody present in a serum of a sweat allergy patient.

In one embodiment, the MGL_1304 partial peptide may release histamine via IgE from a cell expressing the IgE receptor.

The MGL_1304 partial peptide provided by the present invention may be an isolated protein or polypeptide.

In one embodiment, the present invention provides an analog of the MGL_1304 partial peptide. The analog is not particularly limited as long as the analog can be prepared based on a peptide consisting of a portion of the amino acid sequence represented by SEQ ID NO: 1. Examples of the analog of the peptide consisting of a portion of the amino acid sequence represented by SEQ ID NO: 1 include a peptide consisting of an amino acid sequence having 60, 70, 80, 90, or 95% or more identity to an amino acid sequence represented by any of SEQ ID NOs: 2 to 7, and a polypeptide consisting of an amino acid sequence with 1, 2, 3, 4, 5, 6, 7, 8, 9, 10, 11, 12, 13, 14, 15, 16, 17, 18, 19, or 20 amino acids deleted, substituted, or added in an amino acid sequence represented by any of SEQ ID NOs: 2 to 7.

Another example of the analog of the peptide consisting of a portion of the amino acid sequence represented by SEQ ID NO: 1 may be a peptide consisting of an amino acid sequence represented by any of SEQ ID NOs: 2 to 7 to which a tag is added. As used herein, a tag means a portion added to a polypeptide for purification, detection, etc. of the polypeptide and is exemplified by histidine (His), gluta-thione-S-transferase (GST), a maltose-binding protein (MBP), myc, a FLAG tag, Trigger Factor (TF), etc. A polypeptide having a tag added thereto is obtained by expressing the polypeptide by using an expression vector, for example, pET30a (manufactured by Novagen) (for His tags), pGEX (manufactured by GE Healthcare Bio-Sciences Corp.) (for GST tags), and a pCold TF vector (manufactured by TAKARA BIO INC.), in a suitable host cell such as a microorganism and a cell.

These analogs of the MGL_1304 partial peptide can be analogs of peptides binding to IgE antibody present in a serum of a sweat allergy patient.

The analogs of the MGL_1304 partial peptide may release histamine via IgE from a cell expressing IgE receptor.

The analogs of the MGL_1304 partial peptide provided by the present invention may be an isolated protein or polypeptide.

The MGL_1304 partial peptide and the analog thereof provided by the preset invention can be manufactured by a conventional genetic engineering method or a method used in peptide synthesis. For example, the MGL_1304 partial peptide and the analog thereof may be manufactured by the following method:

(i) the MGL_1304 partial peptide provided by the preset invention is expressed in *E. coli* or cells using an expression vector into which a nucleotide encoding an amino sequence represented by any of SEQ ID NOs: 2 to 7 is inserted; or (ii) the MGL_1304 partial peptide provided by the preset invention is expressed in *E. coli* or cells using an expression vector inserted into which a nucleotide encoding an amino sequence having 60, 70, 80, 90, or 95% or more identity to an amino acid sequence represented by any of SEQ ID NOs: 2 to 7 is inserted; or (iii) the MGL_1304 partial peptide provided by the preset invention is expressed in *E. coli* or cells using an expression vector into which a nucleotide encoding an amino sequence with 1, 2, 3, 4, 5, 6, 7, 8, 9, 10, 11, 12, 13, 14, 15, 16, 17, 18, 19, or 20 amino acids deleted, substituted, or added in an amino acid sequence represented by any of SEQ ID NOs: 2 to 7 is inserted.

The MGL_1304 partial peptide and the analog thereof provided by the preset invention bind to IgE antibody and/or IgG antibody binding to a sweat allergy antigen present in a serum of a sweat allergy patient and therefore can be used for detecting, quantifying, neutralizing, or removing IgE antibody and/or IgG antibody binding to a sweat allergy antigen present in a serum of a sweat allergy patient. Thus, in one embodiment, the present invention provides use of the MGL_1304 partial peptide and the analog thereof (e.g., the proteins consisting of an amino acid sequence represented by any of SEQ ID NOs: 2 to 7 and the analogs thereof) in detection, quantification, neutralization, or removal of IgE antibody and/or IgG antibody binding to a sweat allergy antigen.

3. Gene, Vector, and Transformant

In a third aspect, the present invention provides a gene encoding a sweat allergy antigen protein that is a protein derived from a microorganism, the MGL_1304 partial peptide, or an analog thereof.

In one embodiment, the present invention provides a polynucleotide encoding an amino acid sequence represented by any of SEQ ID NOs: 1 to 7.

In one embodiment, the present invention provides a polynucleotide consisting of a nucleotide sequence having 60, 70, 80, 90, or 95% or more identity to a polynucleotide encoding an amino acid sequence represented by any of SEQ ID NOs: 1 to 7, and a polynucleotide consisting of a nucleic acid sequence with 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 bases deleted, substituted, or added in a polynucleotide encoding an amino acid sequence represented by any of SEQ ID NOs: 1 to 7.

The polynucleotide provided by the present invention may be an isolated polynucleotide.

The polynucleotide provided by the present invention can be introduced into a vector and expressed in a host cell as needed.

Therefore, in one embodiment, the present invention provides a vector containing the polynucleotide provided by the present invention, and a host cell (transformant) in which the polynucleotide provided by the present invention is introduced.

The polynucleotide, the vector, and the host cell provided by the present invention can be used in manufacturing of the protein or peptide consisting of an amino sequence represented by any of any of SEQ ID NOs: 2 to 7 or the analog thereof. Therefore, in one embodiment, the present invention provides use of the polynucleotide, the vector, and the host cell provided by the present invention in manufacturing of a sweat allergy antigen.

4. Antibody

In a fourth aspect, the present invention provides an antibody or an antibody fragment specifically binding to a sweat allergy antigen protein that is a protein derived from a microorganism or the MGL_1304 partial peptide.

In one embodiment, the present invention provides an antibody or an antibody fragment specifically binding to a protein encoded by the MGL_1304 gene (e.g., a protein consisting of the amino acid sequence represented by SEQ ID NO: 1), a peptide consisting of an amino acid sequence represented by any of SEQ ID NOs: 2 to 7 and SEQ ID NOs: 10 to 13, or an analog thereof. For example, an antibody or an antibody fragment specifically binding to a protein encoded by the MGL_1304 gene (e.g., a protein consisting of the amino acid sequence represented by SEQ ID NO: 1) can be prepared by administering a protein or a peptide consisting of an amino acid sequence represented by any of SEQ ID NOs: 1 to 7 and 10 to 13 or an analog thereof expressed in E. coli, COS7 cells, or Malassezia globosa as an antigen to a mammal (e.g., a mouse or a rabbit).

In one embodiment, the present invention provides an antibody or an antibody fragment specifically binding to a protein present in a culture supernatant of Malassezia globosa and binding to serum derived from a sweat allergy patient and/or smith2 antibodies. For example, an antibody or an antibody fragment specifically binding to a protein present in a culture supernatant of Malassezia globosa and binding to serum derived from a sweat allergy patient and/or smith2 antibodies can be prepared by administering a protein present in a culture supernatant of Malassezia globosa and binding to serum derived from a sweat allergy patient and/or smith2 antibodies to a mammal (e.g., a mouse or a rabbit) as an antigen.

In one embodiment, the present invention provides a method of manufacturing an antibody or an antibody fragment specifically binding to a protein encoded by the MGL_1304 gene (e.g., a protein consisting of the amino acid sequence represented by SEQ ID NO: 1) comprising administering a protein or a peptide consisting of an amino acid sequence represented by any of SEQ ID NOs: 1 to 7 and 10 to 13 or an analog thereof, or a protein present in a culture supernatant of Malassezia globosa and binding to serum derived from a sweat allergy patient and/or smith2 antibodies, to a mammal (e.g., a mouse or a rabbit).

As used herein, antibodies include polyclonal antibodies and monoclonal antibodies.

As used herein, monoclonal antibodies include genetic recombinant monoclonal antibodies artificially modified for the purpose of reducing heterologous antigenicity to a human, for example, chimera monoclonal antibodies, humanized monoclonal antibodies and human monoclonal antibodies.

A fragment of an antibody is a portion of an antibody specifically binding to an antigen. A fragment of an antibody may be Fab (fragment of antigen binding), F(ab')2, Fab', a single-chain antibody (single chain Fv; hereinafter referred to as scFv), a disulfide stabilized antibody (disulfide stabilized Fv; hereinafter referred to as dsFv), a dimerized V-region fragment (hereinafter referred to as a diabody), and a peptide comprising CDR (Expert Opinion on Therapeutic Patents, Vol. 6, No. 5, pp. 441-456, 1996). The antibodies and the fragments of antibodies can be prepared by a well-known method in the industry (see, e.g., Antibodies: A Laboratory Manual, Cold Spring Harbor Laboratory Press, 1988; http://www.gene.mie-u.ac.jp/Protocol/Original/Antibody.html; U.S. Pat. Nos. 6,331,415, 5,693,761, 5,225,539, 5,981,175, 5,612,205, 5,814,318, 5,545,806, 7,145,056, 6,492,160, 5,871,907, and 5,733,743).

The antibodies provided by the present invention may be used as a tool recognizing a protein consisting of the amino acid sequence represented by SEQ ID NO: 1 present in a sample derived from a human, for example, human sweat or skin, to analyze an amount, distribution, a function, etc. of the protein.

The antibodies provided by the present invention may have a label bound thereto. Examples of the label include an enzyme, a fluorescent substance, a radioisotope, biotin, etc.

Examples of the enzyme include alkaline phosphatase, peroxidase, glucose oxidase, tyrosinase, acid phosphatase, etc.

Examples of the fluorescent substance include fluorescein isothiocyanate (FITC), GFP, luciferin, etc.

Examples of the radioisotope include $^{125}$I, $^{14}$C, $^{32}$P, etc.

Examples of an antibody specifically binding to a sweat allergy antigen protein, i.e., a protein derived from a microorganism, provided by the present invention include, but not limited to, the following (i) to (iii):

(i) an antibody produced by the hybridoma (Mouse-Mouse hybridoma smith-1) of Accession No. FERM BP-11110 (transferred from FERM P-21439) deposited to the International Patent Organism Depositary of the National Institute of Advanced Industrial Science and Technology on Apr. 1, 2009;

(ii) an antibody produced by the hybridoma (Mouse-Mouse hybridoma smith-2) of Accession No. FERM BP-11111 (transferred from FERM P-21440) deposited to the International Patent Organism Depositary of the National Institute of Advanced Industrial Science and Technology on Apr. 1, 2009; and (iii) an antibody produced by the hybridoma (Mouse-Mouse hybridoma smith-8) of Accession No. FERM BP-11112 (transferred from FERM P-21697) deposited to the International Patent Organism Depositary of the National Institute of Advanced Industrial Science and Technology on Apr. 1, 2009.

5. Composition or Kit for Detecting or Quantifying Sweat Allergy Antigen

In a fifth aspect, the present invention provides a composition or kit for detecting a sweat allergy antigen, or a composition or kit for measuring an amount of a sweat allergy antigen, comprising an antibody or an antibody fragment specifically binding to a sweat allergy antigen protein that is a protein derived from a microorganism or the MGL_1304 partial peptide.

The detection of a sweat allergy antigen and the measurement of an amount of a sweat allergy antigen are measured by any method. For example, the detection of sweat allergy antigens and the measurement of an amount of a sweat allergy antigen can be performed using Western blotting or ELISA.

Therefore, in one embodiment, the composition for detecting a sweat allergy antigen or the composition for measuring an amount of a sweat allergy antigen may be a composition comprising an antibody or an antibody fragment specifically binding to a sweat allergy antigen protein that is a protein derived from a microorganism or the MGL_1304 partial peptide for use in Western blotting or ELISA.

In one embodiment, the kit for detecting a sweat allergy antigen or the kit for measuring an amount of a sweat allergy antigen may be a kit comprising a reagent necessary for Western blotting or ELISA. Examples of the reagents necessary for Western blotting include an SDS-PAGE gel, a nitrocellulose membrane or PVDF membrane, the antibody provided in the fourth aspect of the present invention, a blocking solution (e.g., a BSA solution, a milk protein solution), wash solution (phosphate buffer containing a surfactant (e.g., PBS containing Tween20)), a luminescence detection reagent, etc. Examples of the reagents necessary for ELISA include a plate (e.g., a 96-well plate), the antibody provided in the fourth aspect of the present invention, a blocking solution (e.g., a BSA solution, a milk protein solution), wash solution (phosphate buffer containing a surfactant (e.g., PBS containing Tween20)), a chromogenic substrate (e.g., TMB), etc.

The kit for detecting a sweat allergy antigen or the kit for measuring an amount of a sweat allergy antigen may include as a standard a protein encoded by the MGL_1304 gene (e.g., a protein consisting of the amino acid sequence represented by SEQ ID NO: 1) or a protein present in a culture supernatant of *Malassezia globosa* and binding to serum derived from a sweat allergy patient and/or smith2 antibodies. Using a solution at a known concentration of a protein encoded by the MGL_1304 gene (e.g., a protein consisting of the amino acid sequence represented by SEQ ID NO: 1) or a protein present in a culture supernatant of *Malassezia globosa* and binding to serum derived from a sweat allergy patient and/or smith2 antibodies, an amount of a sweat allergy antigen can accurately be quantified. For example, using a plurality of solutions at known concentrations of a protein present in a culture supernatant of *Malassezia globosa* and binding to serum derived from a sweat allergy patient and/or smith2 antibodies, an amount of a sweat allergy antigen can be accurately quantified. The protein encoded by the MGL_1304 gene (e.g., a protein consisting of the amino acid sequence represented by SEQ ID NO: 1) may be prepared by expressing the gene provided in the third aspect of the present invention in a host such as *E. coli* and COS7 cells.

Western blotting and ELISA can be conducted as needed by those skilled in the art.

For example, in the case of Western blotting, a sample containing a sweat allergy antigen is electrophoresed using the SDS-PAGE gel; the electrophoresed sample is transferred to the PVDF membrane; the membrane is reacted with an antibody against the sweat allergy antigen, i.e., the mouse IgG antibody provided in the fourth aspect of the present invention, followed by an enzyme-labeled anti-mouse IgG antibody; and, subsequently, the sweat allergy antigen can be detected or quantified through the enzyme activity.

For example, in the case of ELISA, a sample containing a sweat allergy antigen is coated on a plate by adding the sample to the plate; the coated sample is reacted with an antibody against the sweat allergy antigens, i.e., the mouse IgG antibody provided in the fourth aspect of the present invention, followed by an enzyme-labeled anti-mouse IgG antibody; and, subsequently, the sweat allergy antigen can be detected or quantified through the enzyme activity. In another example, a sweat allergy antigen may be detected or quantified by sandwich ELISA where two types of the antibodies against the sweat allergy antigen provided in the fourth aspect of the present invention are used. Among these reactions, the reaction with the enzyme-labeled anti-mouse IgG antibody may be omitted when the mouse IgG antibody provided in the fourth aspect of the present invention, which is enzymatically labeled, is used.

In one embodiment, the present invention provides a method of detecting a sweat allergy antigen or a method of measuring an amount of a sweat allergy antigen comprising subjecting the antibody provided in the fourth aspect of the present invention to reacting with a sample derived from a human. Examples of a sample derived from a human include, but not limited to, a human sweat, human skin washings, a solution of an extract of human skin, a human serum, a human plasma, etc.

In one embodiment, the present invention provides use of an antibody or an antibody fragment specifically binding to a sweat allergy antigen protein that is a protein derived from a microorganism or the MGL_1304 partial peptide provided in the fourth aspect of the present invention, for manufacturing a composition or kit for detecting a sweat allergy antigen, or a composition or kit for measuring an amount of a sweat allergy antigen.

6. Composition or Kit for Detecting or Quantifying Antibody Binding to Sweat Allergy Antigen In a sixth aspect, the present invention provides a composition or kit for detecting an antibody binding to a sweat allergy antigen, or a composition or kit for measuring an amount of an antibody binding to a sweat allergy antigen, comprising a sweat allergy antigen protein that is a protein derived from a microorganism or the MGL_1304 partial peptide. Examples of the detected or quantified antibodies may be, but not limited to, human IgE antibodies or human IgG antibodies (e.g., all the human IgG antibodies binding to sweat allergy antigens, or human IgG4 antibodies binding to sweat allergy antigens).

The detection of an antibody binding to a sweat allergy antigen and the measurement of an amount of an antibody binding to sweat allergy antigens can be measured by any method. For example, the detection of an antibody binding to a sweat allergy antigen and the measurement of an amount of an antibody binding to a sweat allergy antigen can be performed using Western blotting or ELISA.

Therefore, in one embodiment, the composition for detecting an antibody binding to a sweat allergy antigen or the composition for measuring an amount of an antibody binding to a sweat allergy antigen may be a composition comprising the sweat allergy antigen protein that is a protein derived from a microorganism or the MGL_1304 partial peptide for use in Western blotting or ELISA.

In one embodiment, the kit for detecting an antibody binding to a sweat allergy antigen or the kit for measuring an amount of an antibody binding to a sweat allergy antigen may be a kit comprising a reagent necessary for Western blotting or ELISA. Examples of the reagents necessary for Western blotting include an SDS-PAGE gel, a nitrocellulose membrane or PVDF membrane, the sweat allergy antigen provided in the first aspect of the present invention (e.g., a protein encoded by the MGL_1304 gene (e.g., a protein consisting of the amino acid sequence represented by SEQ ID NO: 1), a protein present in a culture supernatant of *Malassezia globosa* and binding to serum derived from a sweat allergy patient and/or smith2 antibodies) or the MGL_1304 partial peptide provided in the second aspect of the present invention (e.g., a peptide indicated by any of SEQ ID NOs: 2 to 7), a blocking solution (e.g., a BSA solution, a milk protein solution), wash solution (phosphate buffer solution containing a surfactant (e.g., PBS containing Tween20)), a luminescence detection reagent, etc. Examples of the reagents necessary for ELISA include a plate (e.g., a 96-well plate), the sweat allergy antigen provided in the first aspect of the present invention (e.g., a protein coded by the MGL_1304 gene (e.g., a protein consisting of the amino acid sequence represented by SEQ ID NO: 1), a protein present in a culture supernatant of *Malassezia globosa* and binding to serum derived from a sweat allergy patient and/or smith2 antibodies (Accession No. FERM BP-11111)) or the MGL_1304 partial peptide provided in the second aspect of the present invention (e.g., a peptide indicated by any of SEQ ID NOs: 2 to 7), a blocking solution (e.g., a BSA solution, a milk protein solution), wash solution (phosphate buffer solution containing a surfactant (e.g., PBS containing Tween20)), etc.

The kit for detecting an antibody binding to a sweat allergy antigen or the kit for measuring an amount of an antibody binding to a sweat allergy antigen may comprise as a standard a protein encoded by the MGL_1304 gene (e.g., a protein consisting of the amino acid sequence represented by SEQ ID NO: 1) or a protein present in a culture supernatant of *Malassezia globosa* and binding to serum derived from a sweat allergy patient and/or smith2 antibodies. Using a solution at a known concentration of these proteins, an antibody binding to the protein can accurately be quantified. For example, using a plurality of solutions at known concentrations of a protein present in a culture supernatant of *Malassezia globosa* and binding to serum derived from a sweat allergy patient and/or smith2 antibodies, the antibody binding to a sweat allergy antigen can accurately be quantified based on an amount of the antigen.

Western blotting and ELISA can be conducted as needed by those skilled in the art.

For example, in the case of ELISA, the sweat allergy antigen protein provided in the first aspect of the present invention or the MGL_1304 partial peptide provided in the second aspect of the present invention is coated; a sample containing an antibody binding to a sweat allergy antigen is added thereto; the sample is reacted with an enzyme-labeled anti-human antibody (e.g., enzyme-labeled anti-human IgG antibody, enzyme-labeled anti-human IgM antibody, enzyme-labeled anti-human IgG4 antibody); and the enzyme activity can be measured to detect or quantify the sweat allergy antigen. In another example, the antibody against a sweat allergy antigen provided in the fourth aspect of the present invention is coated; the antibody is reacted with the sweat allergy antigen protein provided in the first aspect of the present invention or the MGL_1304 partial peptide provided in the second aspect of the present invention; a sample containing an antibody binding to a sweat allergy antigen is added thereto; the sample is reacted with enzyme-labeled anti-human antibody (e.g., enzyme-labeled anti-human IgG antibody, enzyme-labeled anti-human IgM antibody, enzyme-labeled anti-human IgG1 antibody); and the enzyme activity may be measured to detect or quantify the sweat allergy antigen.

In one embodiment, the present invention provides a method of detecting an antibody binding to a sweat allergy antigen or a method of measuring an amount of an antibody binding to a sweat allergy antigen comprising subjecting the sweat allergy antigen provided in the first aspect of the present invention or the MGL_1304 partial peptide provided in the second aspect of the present invention to reacting with a sample derived from a human. The method may be performed in vitro. Examples of the sample derived from a human include, but not limited to, a human sweat, human skin washings, a solution of an extract of human skin, a human serum, a human plasma, etc.

In one embodiment, the present invention provides use of the sweat allergy antigen protein provided in the first aspect of the present invention or the MGL_1304 partial peptide provided in the second aspect of the present invention, for manufacturing a composition or kit for detecting an antibody binding to a sweat allergy antigen, or a composition or kit for measuring an amount of an antibody binding to a sweat allergy antigen.

7. Composition or Kit for Diagnosing Sweat Allergy or Disease Related to Sweat Allergy Antigen In a seventh aspect, the present invention provides a composition or kit for diagnosing a sweat allergy or a disease related to a sweat allergy antigen, comprising:
(i) the sweat allergy antigen protein that is a protein derived from a microorganism or the MGL_1304 partial peptide; or
(ii) an antibody or an antibody fragment specifically binding to the sweat allergy antigen protein that is a protein derived from a microorganism or the MGL_1304 partial peptide.

As used herein, a disease related to a sweat allergy antigen may be a disease accompanied with a sweat allergy induced by an antigenic substance contained in sweat and may be, for example, atopic dermatitis, urticaria (e.g., cholinergic urticaria), allergic rhinitis, etc.

The composition or kit for diagnosing a sweat allergy or a disease related to a sweat allergy antigen provided in the seventh aspect of the present invention can diagnose, or assist the diagnosis of, a sweat allergy or a disease related to a sweat allergy antigen through detection or quantification of the antibody binding to a sweat allergy antigen or the sweat allergy antigen.

In one embodiment, the composition or kit for detecting or quantifying an antibody binding to a sweat allergy antigen provided in the sixth aspect of the present invention is available for the composition or kit, relating to the seventh aspect of the present invention, for diagnosing a sweat allergy or a disease relating to a sweat allergy antigen comprising (i) the sweat allergy antigen protein that is a protein derived from a microorganism or the MGL_1304 partial peptide. For example, an amount of an antibody (e.g., IgE and/or IgG (e.g., all the IgGs and/or IgG4)) binding to a sweat allergy antigen in a sample (e.g., serum or plasma) derived from blood of a human subject is measured by using the kit provided in the sixth aspect of the present invention, and is compared with an amount of an antibody binding to a sweat allergy antigen in a sample derived from blood of a healthy person, and if the amount of an antibody binding to the sweat allergy antigens in the sample derived from blood of the subject is larger than the amount of an antibody binding to the sweat allergy antigen in the sample derived from blood of a healthy person, the subject can be diagnosed with a sweat allergy or a disease related to a sweat allergy antigen, or having a risk of a sweat allergy or a disease related to a sweat allergy antigen. Alternatively, this measurement result of an amount of an antibody binding to the sweat allergy antigen can be used for assisting a diagnosis of a sweat allergy or a disease relating to a sweat allergy antigen from clinical finding.

In one embodiment, the composition or kit for detecting a sweat allergy antigen, or the composition or kit for measuring an amount of a sweat allergy antigen, provided in the fifth aspect of the present invention is available for the composition or kit, relating to the seventh aspect of the present invention, for diagnosing a sweat allergy or a disease related to a sweat allergy antigen comprising (ii) an antibody or an antibody fragment specifically binding to the sweat allergy antigen protein that is a protein derived from a microorganism or the MGL_1304 partial peptide. For example, an amount of a sweat allergy antigen in a sample of sweat of a human subject is measured by the kit provided in the fifth aspect of the present invention, and is compared with an amount of a sweat allergy antigen in a sample of sweat of a healthy person, and if the amount of a sweat allergy antigen in the sweat of the subject is larger than the amount of an sweat allergy antigen in the sweat of a healthy person, the subject can be diagnosed with a sweat allergy or a disease related to a sweat allergy antigen, or having a risk of a sweat allergy or a disease related to a sweat allergy antigen. Alternatively, this measurement result of an amount of a sweat allergy antigen can be used for assisting a diagnosis of a sweat allergy or a disease relating to a sweat allergy antigen from clinical finding.

The kit for diagnosing a sweat allergy or a disease relating to a sweat allergy antigen provided in the seventh aspect of the present invention may comprise as a standard a protein encoded by the MGL_1304 gene (e.g., a protein consisting of the amino acid sequence represented by SEQ ID NO: 1) or a protein present in a culture supernatant of *Malassezia globosa* and binding to serum derived from a sweat allergy patient and/or smith2 antibodies. Use of this standard enables accurate quantification and enables an accurate diagnosis.

In one embodiment, the present invention provides a kit or composition for a skin test comprising (i) a sweat allergy antigen protein that is a protein derived from a microorganism or the MGL_1304 partial peptide. The skin test may be, for example, a patch test, a scratch test, a prick test, or an intradermal test. The skin test may enable to diagnose a subject with a sweat allergy or a disease relating to a sweat allergy or having a risk thereof, or the skin test may provide data for assisting the diagnosis.

The kit for a skin test may further comprise a saline used as a comparative control.

The patch test is widely performed as a simple method of examination for a contact allergy in the dermatological field. Since the presence of a contact allergy leads to sensitization of not only a portion of dermatitis but also the whole body skin, a cause of contact dermatitis can be determined by artificially reproducing allergic contact dermatitis on a healthy skin. For example, the sweat allergy antigen protein or the MGL_1304 partial peptide (e.g., a protein consisting of an amino acid sequence represented by any of SEQ ID NOs: 1 to 7) provided in the first or second aspect of the present invention is dripped or applied to an adhesive tape, and the adhesive tape is affixed to the back, the upper arm, the thigh, etc. The determination is made after two days, three days, and one weak in accordance with the ICDRG (International Contact Dermatitis Research Group) scale.

The determination is indicated by (−) when no reaction exists, (+) when a reagent portion of the adhesive tape is associated with erythema and edema, or (++) or (+++) depending on a degree of the reaction.

The scratch test and the prick test are examinations performed by dropping an antigen solution onto a skin surface, making a scratch on the skin with a needle tip such that bleeding does not occur, and examining a reaction after 15 to 20 minutes. If the antigen-specific IgE antibody exists on a surface of a mast cell in an upper layer of the dermis, the antibody reacts with the dropped antigen, and histamine and chemical transmitters in the mast cell are released, resulting in a red swollen spot. For example, the sweat allergy antigen protein or the MGL_1304 partial peptide (e.g., a protein consisting of an amino acid sequence represented by any of SEQ ID NOs: 1 to 7) provided in the first or second aspect of the present invention can be used as an antigen for the scratch test and the prick test.

The test for intracutaneous reactivity is a test performed by injecting an extremely small amount of antigen solution inside a thin skin and observing whether the injected portion becomes red and swollen after a certain time so as to determine the presence of an allergy. For example, the sweat allergy antigen protein or the MGL_1304 partial peptide (e.g., a protein consisting of an amino acid sequence represented by any of SEQ ID NOs: 1 to 7) provided in the first or second aspect of the present invention can be used as the antigen for the intradermal test.

In another embodiment, the present invention provides a kit or composition for a histamine release test comprising (i) the sweat allergy antigen protein that is a protein derived from a microorganism or the MGL_1304 partial peptide. In the histamine release test, a cell reaction is used to measure an amount histamine release from blood cells (basophils) due to antigen stimulation. For example, an amount of histamine released from blood cells (basophils) due to antigen stimulation may allow a diagnosis of a sweat allergy or a disease relating to a sweat allergy or having a risk thereof, or may provide data assisting the diagnosis.

The kit for a histamine release test may further comprise an anti-histamine antibody and histamine as a standard.

In one embodiment, the present invention provides a method of diagnosing, or assisting diagnosis of, a sweat allergy or a disease relating to a sweat allergy antigen, comprising contacting
(i) the sweat allergy antigen protein that is a protein derived from a microorganism or the MGL_1304 partial peptide provided in the first or second aspect of the present invention, or
(ii) an antibody or an antibody fragment specifically binding to the sweat allergy antigen protein that is a protein derived from a microorganism or the MGL_1304 partial peptide provided in the fourth aspect of the present invention
with a sample derived from a human (a blood sample (e.g., plasma, serum), sweat, a sample derived from skin (e.g., skin washings)). The method may be performed in vitro.

In one embodiment, the present invention provides use of
(i) the sweat allergy antigen protein that is a protein derived from a microorganism or the MGL_1304 partial peptide provided in the first or second aspect of the present invention, or
(ii) an antibody or an antibody fragment specifically binding to the sweat allergy antigen protein that is a protein derived from a microorganism or the MGL_1304 partial peptide provided in the fourth aspect of the present invention for manufacturing the composition for diagnosing, or assisting diagnosis of, a sweat allergy or a disease relating to a sweat allergy antigen.

8. Composition for Treating Sweat Allergy or Disease Relating to Sweat Allergy Antigen In an eighth aspect, the present invention provides a therapeutic composition for a sweat allergy or a disease relating to a sweat allergy antigen comprising a sweat allergy antigen protein that is a protein derived from a microorganism or the MGL_1304 partial peptide.

The therapeutic composition for a sweat allergy or a disease relating to a sweat allergy antigen may be a composition for a hyposensitization therapy. The "hyposensitization therapy" is a method of treatment performed by administering a slight amount of a therapeutic allergen for an allergy associated with IgE antibody in a gradually increasing amount at intervals of a certain number of days so as to avoid occurrence of an allergic reaction even when a causative allergen enters. The protein or the peptide provided in the first or second aspect of the present invention may be used as the therapeutic allergen in the hyposensitization therapy.

The therapeutic composition provided by the present invention is appropriately formulated using the protein or the peptide provided by the present invention. For example, the therapeutic composition provided by the present invention can be formulated with pharmaceutically acceptable carriers (including additives). The pharmaceutically acceptable carriers include, but not limited to, excipients (e.g., dextrin, hydroxypropyl cellulose, and polyvinylpyrrolidone), disintegrators (e.g., carboxymethyl cellulose), lubricants (e.g., magnesium stearate), surfactants (e.g., sodium lauryl sulfate), solvents (e.g., water, saline, and soybean oil), and preservatives (e.g., p-hydroxybenzoic acid ester).

A dosage and an administration method of the therapeutic composition may appropriately be selected by those skilled in the art depending on an age, a body weight, and a health condition of a subject to be administered.

In one embodiment, the present invention provides a method of treating a sweat allergy or a disease relating to a sweat allergy antigen comprising administering the sweat allergy antigen protein that is a protein derived from a microorganism or the MGL_1304 partial peptide provided in the first or second aspect of the present invention.

In one embodiment, the present invention provides use of the sweat allergy antigen protein that is a protein derived from a microorganism or the MGL_1304 partial peptide provided in the first or second aspect of the present invention for manufacturing a therapeutic composition for a sweat allergy or a disease relating to a sweat allergy antigen.

9. Composition for Removing or Neutralizing Sweat Allergy Antigen and Material for Removing Sweat Allergy Antigen In a ninth aspect, the present invention provides a composition for removing or neutralizing a sweat allergy antigen and a material for removing a sweat allergy antigen comprising a sweat allergy antigen protein that is a protein derived from a microorganism or the MGL_1304 partial peptide.

An antibody specifically binding to the sweat allergy antigen protein or the MGL_1304 partial peptide can be used for neutralizing the antigen activity of the sweat allergy antigen. The antibody can be also used for removing the sweat allergy antigen from an affected part.

For example, an isotonic solution such as a saline comprising an antibody specifically binding to the sweat allergy antigen protein or the MGL_1304 partial peptide may be contacted with the affected part to neutralize the sweat allergy antigen and/or to achieve removable of the sweat allergy antigen.

The antibody specifically binding to the sweat allergy antigen protein or the MGL_1304 partial peptide may be immobilized to fibers and used as a material for removing the sweat allergy antigen from the affected part. An example of the material for removal is a wiping sheet. The material for removal can appropriately be manufactured by those skilled in the art.

For example, Japanese Patent No. 3642340 discloses a method of manufacturing a material for removal such as a wiping sheet comprising immobilizing an antibody to fibers (woven fabric or nonwoven fabric) with an official moisture regain of 7% or more.

Examples of a method of immobilizing an antibody to a carrier such as fibers include a method in which after the carrier is silanized using γ-aminopropyltriethoxysilane etc., an aldehyde group is introduced to a carrier surface by means of glutaraldehyde etc. to covalently bind the aldehyde group and the antibody; a method in which an untreated carrier is immersed in an aqueous solution of the antibody to immobilize the antibody to the carrier though ion binding; a method in which an aldehyde group is introduced to a carrier having a certain functional group to covalently bind the aldehyde group and the antibody; a method in which the antibody is subjected to ion-binding to a carrier having a certain functional group; and a method in which after a carrier is coated with a polymer having a certain functional group, an aldehyde group is introduced to covalently bind the aldehyde group and the antibody. The certain functional group as described above may be an NHR group (R is an alkyl group of any of methyl, ethyl, propyl, and butyl other than H), an $NH_2$ group, a $C_6H_5NH_2$ group, a CHO group, a COOH group, and an OH group. The antibody may be supported via a linker on the carrier, and examples of the linker used include maleimide, NHS (N-Hydroxysuccinimidyl) ester, imidoester, EDC (1-Etyl-3-[3-dimetylaminopropyl]carbodiimido) and PMPI (N-[p-Maleimidophenyl]isocyanete).

The material for removal may be impregnated with water containing glycerol to be stored.

In one embodiment, the present invention provides a method of removing or neutralizing a sweat allergy antigen comprising contacting the antibody specifically binding to the sweat allergy antigen protein or the MGL_1304 partial peptide provided in the fourth aspect of the present invention with the sweat allergy antigen.

In one embodiment, the present invention provides use of the antibody specifically binding to the sweat allergy antigen protein or the MGL_1304 partial peptide provided in the fourth aspect of the present invention for manufacturing a composition for removing or neutralizing a sweat allergy antigen or a material for removing a sweat allergy antigen.

10. Composition or Kit for Determining Effect of Hyposensitization Therapy

In a tenth aspect, the present invention provides a composition or kit for determining an effect of a hyposensitization therapy comprising a sweat allergy antigen protein that is a protein derived from a microorganism or the MGL_1304 partial peptide.

The hyposensitization therapy can be performed by administering a composition comprising a sweat allergy antigen (e.g., the protein provided in the first aspect or the peptide provided in the second aspect of the present invention) in a gradually increasing amount as described in the eighth aspect of the present invention.

In general, it is known that the blood concentration of IgG4 against the antigen is increased while the blood concentration of IgE against the antigen is decreased in the course of treatment in the hyposensitization therapy.

Also in the hyposensitization therapy performed by administering a composition comprising a sweat allergy antigen (e.g., the protein provided in the first aspect or the peptide provided in the second aspect of the present invention) in a gradually increasing amount at intervals of a certain number of days, if the administration shows therapeutic effects, the blood concentration of IgG4 against the sweat allergy antigen may be increased, and the blood concentrations of IgE antibody and total IgG antibody against the sweat allergy antigen may be decreased in the course of treatment.

Therefore, in one embodiment, the present invention provides a method of determining an effect of a hyposensitization therapy comprising measuring an amount of a human IgG4 antibody binding to a sweat allergy antigen (e.g., the protein provided in the first aspect or the peptide provided in the second aspect of the present invention) in a human blood sample (e.g., human serum or plasma). In one embodiment, the present invention provides a method of determining an effect of a hyposensitization therapy comprising comparing an amount of a human IgG4 antibody binding to a sweat allergy antigen (e.g., the protein provided in the first aspect or the peptide provided in the second aspect of the present invention) in a blood sample collected before performing the hyposensitization therapy with a blood sample collected after performing the hyposensitization therapy. In these methods of determining an effect of a hyposensitization therapy, if the concentration of IgG4 antibody binding to a sweat allergy antigen in blood of a patient increases, it can be determined that the hyposensitization therapy exerts an effect. The methods of determining an effect of a hyposensitization therapy may further comprise measuring the amounts of IgE antibody and/or total IgG antibody in the blood to the sweat allergy antigens, and/or comparing the amounts of the IgE antibody and/or total IgG antibody binding to the sweat allergy antigen in a blood sample collected before performing the hyposensitization therapy with a blood sample collected after performing the hyposensitization therapy. The methods of determining an effect of a hyposensitization therapy may be performed in vitro.

The composition or kit for detecting or quantifying an antibody binding to a sweat allergy antigen provided in the sixth aspect of the present invention can be utilized in the measurement of an amount of an antibody binding to the sweat allergy.

Therefore, the composition or kit comprising a sweat allergy antigen protein that is a protein derived from a microorganism or the MGL_1304 partial peptide provided in the sixth aspect of the present invention can be used as a composition or kit for determining an effect of a hyposensitization therapy.

In one embodiment, the present invention provides use of a sweat allergy antigen protein that is a protein derived from a microorganism provided in the first aspect of the present invention or the MGL_1304 partial peptide provided in the second aspect of the present invention for manufacturing a composition or kit for determining an effect of a hyposensitization therapy.

The present invention will hereinafter further be described in examples and these examples are not intended to limit the present invention.

EXAMPLES

Example 1

Purification of Partially Purified Sweat Antigen (QRX)

1-1. Preparation of Concentrated Sweat

After insolubles were removed from a human sweat through 100-μm and 70-μm mesh filters (Nylon Cell Strainers, Falcon), precipitates were further removed by a 0.22-μm filter (Bottle Top Filter, 1 L, Corning). Four litters of the sweat filtrated by the filters were concentrated by ultrafiltration (3000M.W.cut) to about 150 mL and used as a material for the sweat antigen purification.

1-2. Separation by Means of Anion-Exchange Column

To an anion-exchange column MonoQ 10/100 GT (GE Healthcare Bio-Sciences) preliminarily equilibrated by 10 mmol/L Tris-HCl (pH 8.0), 75 mL of the concentrated sweat prepared at pH 8.0 was loaded, and was eluted through 0 to 1.0 M NaCl concentration gradient in 10 mmol/L Tris-HCl (pH 8.0). AKTA Explorer (GE Healthcare Bio-Sciences) was used as a chromatographic device for purification.

To select a fraction containing a substance inducing the histamine release activity, a histamine release test using basophils of an atopic dermatitis patient was performed for each of fractions.

First, each of the appropriately diluted fractions was mixed at 1:1 with a basophil fraction of an atopic dermatitis patient prepared in a HEPES buffer containing 5 mmol/L glucose, 0.03 w/v % HSA, 2 mmol/L $CaCl_2$, and 1 mmol/L $MgCl_2$, and was incubated at 37° C. for 40 minutes. After supernatant and sedimented blood cells were separated by centrifugation and were respectively denatured by adding 0.2 mol/L perchloric acid, a histamine concentration in the supernatant obtained by the centrifugation was measured by HPLC (Shimadzu LC solution). A rate of the histamine amount of the supernatant relative to the total histamine amount was defined as the histamine release activity.

The histamine amount was measured in accordance with a method described in a literature (Koro, O. et al., J. Allergy Clin. Immunol., 103, 663-670, 1999).

As a result, a fraction eluted within a salt concentration range of 0.25 to 0.3 mol/L NaCl having the histamine release activity higher than the other fractions was recovered as a fraction exhibiting the histamine release activity.

1-3. Separation by Means of Reverse-Phase Column

After diluting 18 mL of the fraction acquired in Example 1-2 with pure water 10 times, TFA was added at a final concentration of 0.1 v/v %. This was loaded to a reverse-phase column (SOURCE 15RPC ST 4.6/100 (GE Healthcare Bio-Sciences)) and was eluted through concentration gradient from 0.1 v/v % TFA/distilled water to 0.1 v/v % TFA/acetonitrile. AKTA Explorer (GE Healthcare Bio-Sciences) was used as a chromatographic device for purification.

After volatilizing TFA and acetonitrile of the eluted fractions, the histamine release test was performed as in Example 1-2.

As a result, a fraction within a range of about 30 to 35 v/v % acetonitrile having the histamine release activity higher than the other fractions was recovered as the fraction exhibiting the histamine release activity (4 mL).

1-4. Separation by Means of Gel Filtration Chromatography

After lyophilization, the fraction obtained in Example 1-3 was re-dissolved in PBS, loaded to Superdex 75 PC 3.2/30 (GE Healthcare Bio-Sciences), and fractionated and eluted in PBS (−). Smart System (GE Healthcare Bio-Sciences) was used as a chromatographic device for purification.

The histamine release test was performed for the eluted fractions as in Example 1-2.

As a result, a fraction within a range of elution positions from 15 to 60 kD was recovered as the fraction exhibiting the histamine release activity (1.2 mL) and subsequently defined as a QRX fraction.

Example 2

Purification and Mass Spectrometry of Partially Purified Sweat Antigen (QRX)

The partially purified sweat antigen (QRX) was purified by using an Aqua 5μ-C18-200A HPLC column (manufactured by Phenomenex) (eluted through concentration gradient from 0.1 v/v % TFA/distilled water to 0.1 v/v % TFA/100% acetonitrile). The fraction exhibiting the histamine release activity was recovered and further purified by a Jupiter 5μ-C18-300A HPLC column (manufactured by Phenomenex) (eluted through concentration gradient from 0.1 v/v % TFA/distilled water to 0.1 v/v % TFA/80% acetonitrile), and a mass spectrometry (TOF-MS) was performed for the fraction exhibiting the histamine release activity (fraction of an arrow of FIG. 1). Although a sample is normally cationized in TOF-MS, the mass measurement was performed through anionization in this experiment. The histamine release activity was measured in accordance with a method described in Koro, O. et al., J. Allergy Clin. Immunol., 103, 663-670, 1999. The detected amino acid sequence matched MGL_1304.

Example 3

Preparation of Recombinant Protein of MGL_1304 and Reactivity to Atopic Dermatitis Patient IgE

Figure 2:
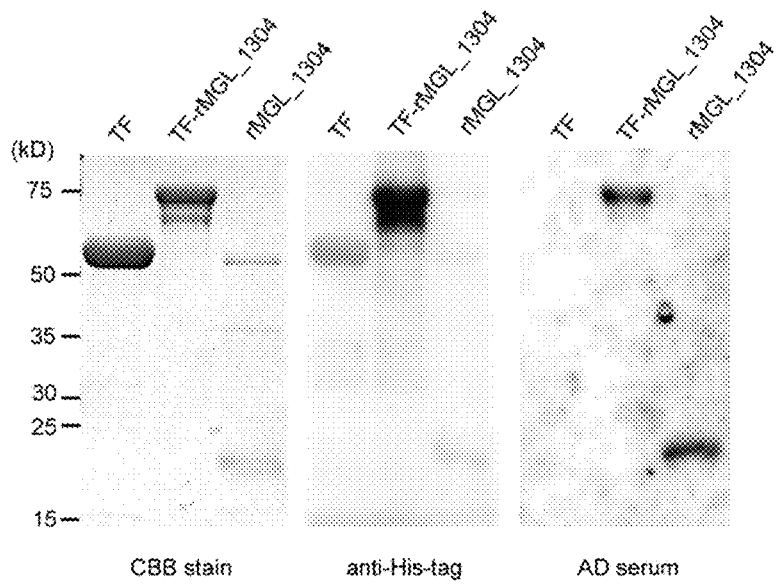
FIG. 2 shows CBB staining and Western blotting analysis of the recombinant protein using an atopic dermatitis patient serum and an anti-his tag antibody.

*Malassezia globosa* was purchased from ATCC (MYA-4612). Reverse transcription of mRNA extracted from *Malassezia globosa* to cDNA was performed and the cDNA encoding MGL_1304 was amplified by PCR (sense primer: 5'-GGGGTACCGTATCCCTCAACATTTTCTCAGCTGC-3' (SEQ ID NO: 8); antisense primer: 5'-CCCAAGCTTT-TAGCAGTCGTACTTGCCGGGGATG-3' (SEQ ID NO: 9), (94° C., 5 min/60° C., 1 min/72° C., 1 min)×1 cycle, (94° C., 1 min/60° C., 1 min/72° C., 1 min)×30 cycles, (94° C., 5 min/60° C., 1 min/72° C., 10 min)×1 cycle) and the amplified cDNA was inserted into the p Cold TF vectors (manufactured by TAKARA BIO INC.) followed by transfection of *E. coli* JM109 with the obtained vector. After culturing at 15° C. for 24 hours, the resulting *E. coli* was dissolved in xTractor buffer and a recombinant protein was purified by a cobalt column. A protein with Trigger Factor only (TF), a TF-MGL_1304 fusion protein (TF-MGL_1304), and a protein obtained by removing TF from the fusion protein through enzyme treatment (rMGL_1304) were prepared. The obtained proteins were subjected to acrylamide gel electrophoresis and were directly CBB-stained (left side of FIG. 2) or transferred to PVDF membranes for immunoblotting with an anti-His tag antibody (center of FIG. 2) and an atopic dermatitis patient serum (right side of FIG. 2). The results indicate that the atopic dermatitis patient IgE binds to rMGL_1304 (FIG. 2).

Figure 3:
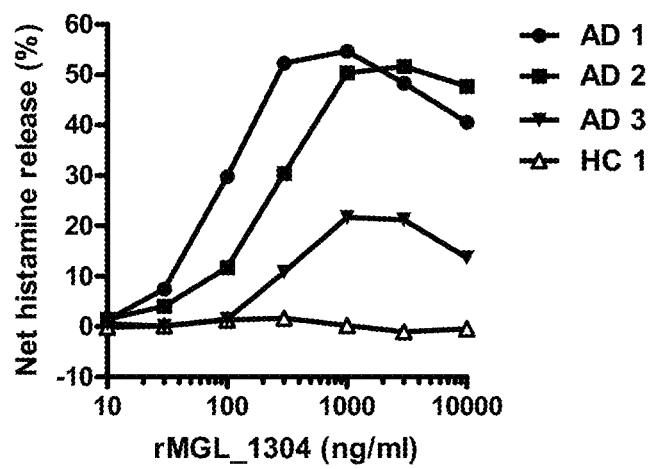
FIG. 3 shows a histamine release assay of atopic dermatitis patients (AD1, AD2, and AD3) and a healthy person (HC1) for the recombinant protein of MGL_1304.

The prepared rMGL_1304 was reacted with atopic dermatitis patient peripheral blood basophils (FIG. 3, AD1, AD2, and AD3) and healthy person peripheral blood basophils (FIG. 3, HC1) to perform the histamine release test. The results indicated that MGL_1304 induces histamine release specifically in the atopic dermatitis patients.

Figure 11:
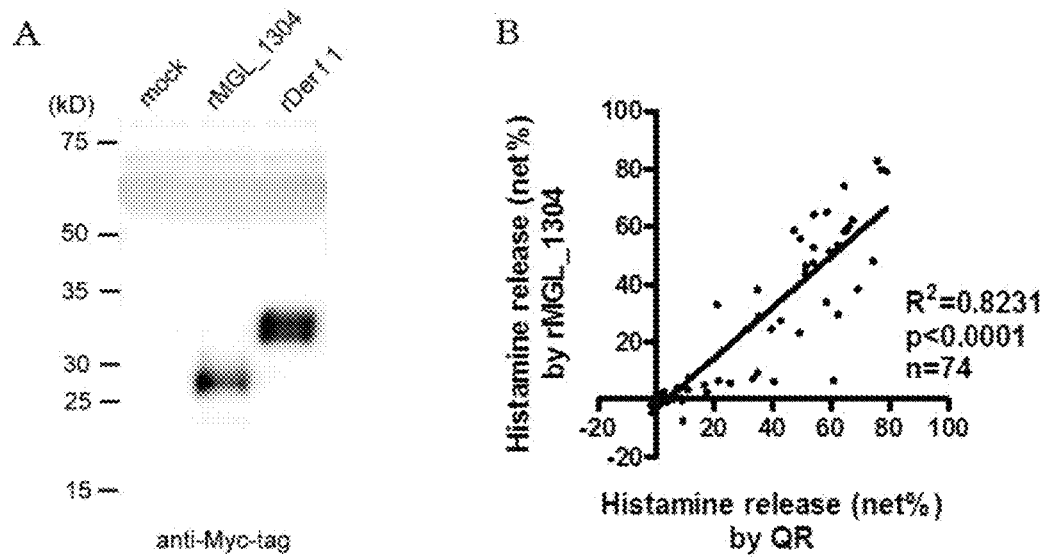
In FIG. 11, A shows Western blotting results when an MGL_1304 gene or a mite antigen gene fused with Myc-tag was expressed in COS7 cells and a culture supernatant thereof was electrophoresed to perform Western blotting using an anti-Myc antibody.

Additionally, cDNA encoding the MGL_1304 described above or mite cDNA is inserted into pSecTag2/Hygro vector (manufactured by Invitrogen) containing Myc-tag to transfect COS7 cells. A culture supernatant of the COS7 cells transfected with these DNAs was subjected to acrylamide gel electrophoresis and transferred to a PVDF membrane for immunoblotting with anti-Myc tag antibodies. The results indicated that the culture supernatant contains proteins corresponding to respective cDNAs (In FIG. 11, A). The culture supernatant was further reacted with atopic dermatitis patient peripheral blood basophils to perform the histamine release test. The same basophils were reacted with sweat antigens (QR) partially purified from the concentrated human sweat by the anion-exchange column chromatography and the reverse-phase column chromatography to perform the histamine release test for comparison with the histamine release rate from the culture supernatant (In FIG. 11, B).

The results indicated that MGL_1304 protein (rMGL_1304) produced by the COST cells induces histamine release like the partially purified human sweat antigens (QR).

Example 4

Reactivity Between Recombinant Protein of MGL_1304 and Atopic Dermatitis Patient IgE Experiments were conducted to study whether MGL_1304 had substantially the same property as the partially purified sweat antigen (QRX) used so far.

(1)

Figure 4:
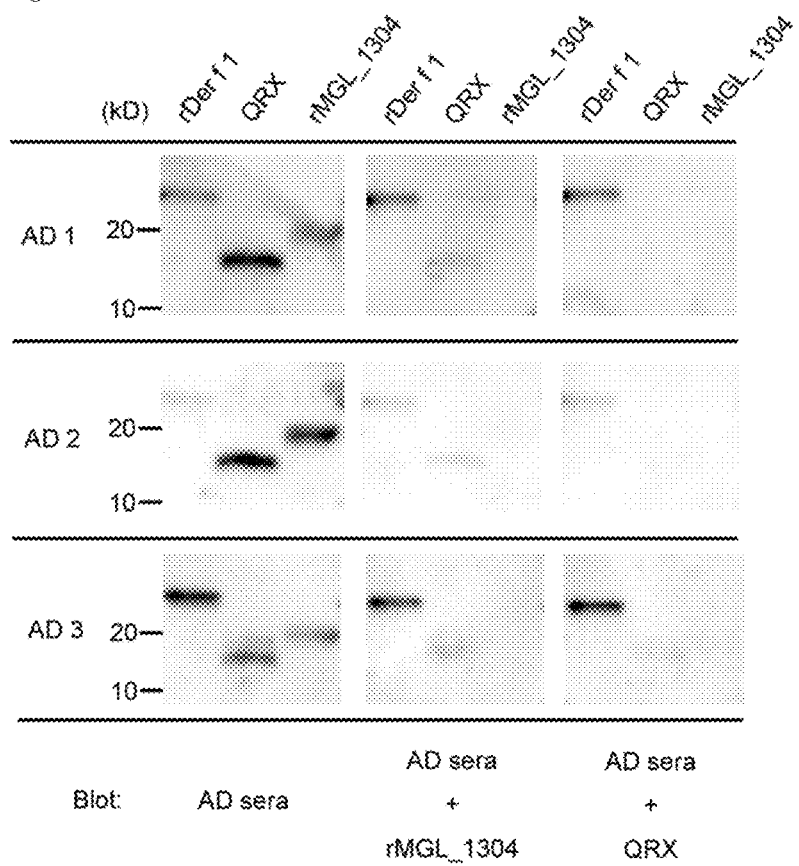
FIG. 4 shows that pretreatment of atopic dermatitis patient serum with one of QRX and MGL_1304 leads to neutralization of binding of antibody with the other one, respectively.

Recombinant mite antigens (Der f1), QRX, and MGL_1304 were electrophoresed and transferred to PVDF membranes to prepare a plurality of membranes. An atopic patient serum (AD serum) pretreated with QRX or MGL_1304 prepared in Example 3 or AD serum without pretreatment was used for immunoblotting. The atopic dermatitis patient serum used was obtained from three patients. The pretreatment with MGL_1304 inhibited the binding of IgE to QRX and the pretreatment with QRX inhibited the binding of IgE to MGL_1304 (FIG. 4).

(2)

Figure 5:
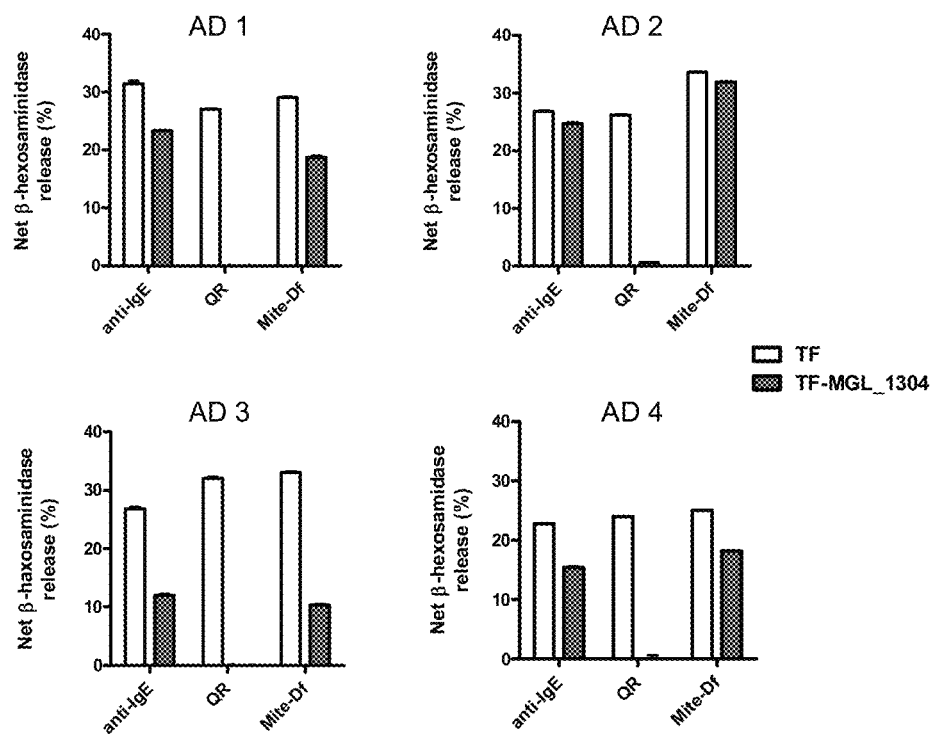
FIG. 5 shows that when atopic dermatitis patient serum is pretreated with MGL_1304 in a reaction system where the atopic dermatitis patient serum is reacted with a rat mast cell line expressing a human high-affinity IgE receptor to sensitize a cell (to provide sensitivity to an antigen), a reactivity (ability of histamine release) of the sensitized cell to QRX disappeared.

The atopic dermatitis patient serums (AD1 to AD4) were pretreated with TF or TF-MGL_1304 and used for sensitizing a rat cell line expressing human IGE receptors (sub-unit A) so as to measure degranulation when being stimulated with anti-IgE, QRX, and a mite extract (Mite-Df). The results indicated that when MGL_1304 specific IgE is removed by pretreatment with MGL_1304 prepared in Example 3, the reactivity to QRX stimulation disappears (FIG. 5).

Example 5

Structure Necessary for IgE Binding in MGL_1304

Figure 6:
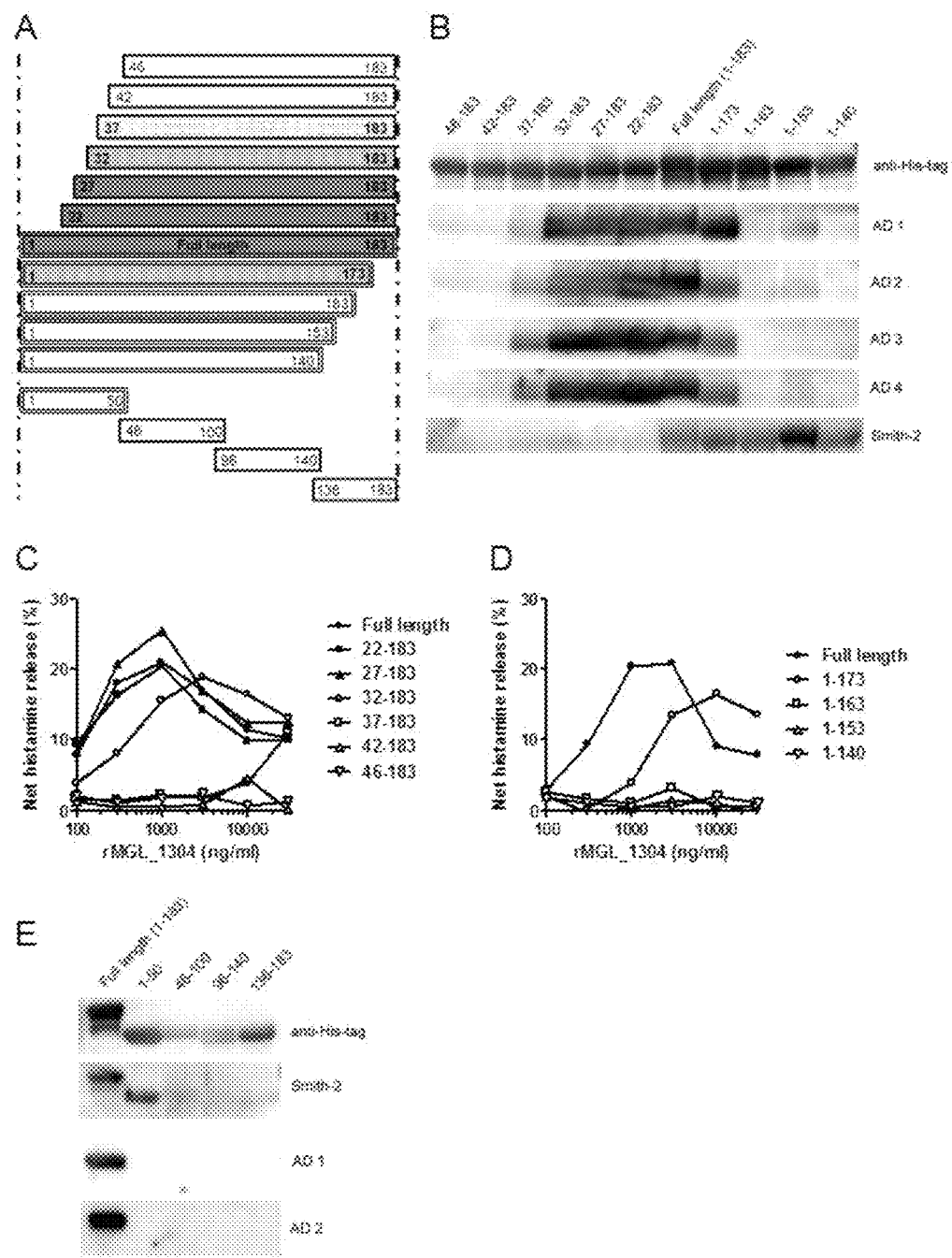
In FIG. 6, A shows a prepared N-terminal or C-terminal truncated protein of MGL_1304.

MGL_1304 proteins (183 amino acids) truncated at the N-terminal, truncated at the C-terminal, and corresponding to 1-50 (P1), 46-100 (P2), 96-140 (P3), and 146-183 (P4) of the polypeptide represented by SEQ ID NO:1 were expressed in *E. coli* to be prepared, and immunoblotted with anti-His tag antibodies, atopic dermatitis patient serums (In FIG. 6, B; AD1, AD2, AD3, and AD4), and/or the Smith2 antibodies, which are antibodies produced by the hybridoma (Mouse-Mouse hybridoma smith-2) of Accession No. FERM BP-11111 (transferred from FERM P-21440) deposited to the International Patent Organism Depositary of the National Institute of Advanced Industrial Science and Technology (Central 6, 1-1-1 Higashi, Tsukuba, Ibaraki 305-8566) on Apr. 1, 2009. For peptide fragments, the histamine release test was performed using the atopic dermatitis patient basophils (In FIGS. 6, C and D). Numbers denote the numbers of the amino acid sequences.

The results indicated that the protein with the N-terminal shortened by 32 or more amino acids or with the C-terminal deleted by 10 or more amino acids loses the binding ability to the atopic dermatitis patient IgE. Neither the binding ability to the atopic dermatitis patient IgE nor the histamine release activity was shown by polypeptides P1 to P4 prepared by fragmenting MGL_1304 polypeptide into four pieces having a short overlap with each other (P1: a polypeptide corresponding to the amino acid sequence 1-50 of the MGL_1304 protein (SEQ ID NO: 10); P2: a polypeptide corresponding to the amino acid sequence 46-100 of the MGL_1304 protein (SEQ ID NO: 11); P3: a polypeptide corresponding to the amino acid sequence 96-140 of the MGL_1304 protein (SEQ ID NO: 12); P4: a polypeptide corresponding to the amino acid sequence 136-183 of the MGL_1304 protein (SEQ ID NO: 13). On the other hand, the Smith-2 antibody exhibits the binding property to both the MGL_1304 protein and the polypeptide (P1) corresponding to the amino acid sequence 1-50 thereof (In FIG. 6, E). These results indicated that the atopic dermatitis patient IgE has a high possibility of recognizing a higher-order structure rather than a short peptide constituting the MGL_1304 protein (In FIG. 6, A). The results also indicated that the P1 (MGL_1304 protein and the polypeptide corresponding to the amino acid sequence 1-50 thereof) region may be a recognition site of an anti-MGL_1304 protein antibody in the MGL_1304 protein.

Example 6

Figure 7:
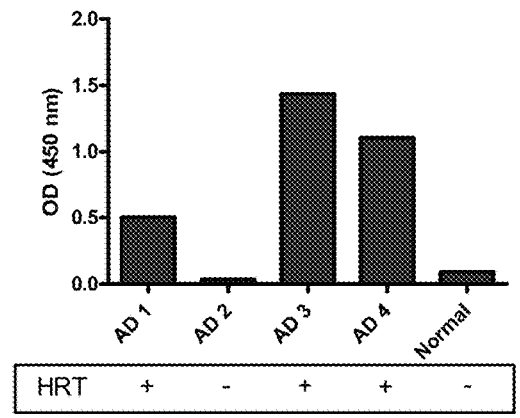
FIG. 7 shows that binding of MGL_1304 recombinant protein with IgE derived from serum of atopic dermatitis patients or healthy volunteer was determined by ELISA, indicating that presence or absence of the binding is consistent with a reactivity of basophils of the serum donor to purified sweat antigens.

ELISA Using MGL_1304 rMGL_1304 prepared in Example 3 was coated onto a 96-well microplate, followed by blocking using bovine serum albumin (BSA), and subsequently, serums of 4 AD patients (including AD2 who is HRT-negative) and a healthy volunteer (Normal) were added thereto. The results of detecting IgE binding to rMGL_1304 with the anti-human IgE antibody are shown (FIG. 7). It was revealed that use of a recombinant MGL_1304 protein allows measurements of MGL_1304-specific IgE in serum (FIG. 7).

Example 7

Immunoreactivity of *Malassezia* Fungus Body (*M. globosa*) Extract, *Malassezia* Fungus Body Culture Supernatant, QRX, and Recombinant MGL_1304 Protein

*M. Globosa* was cultured in a 2693 mDixon medium at 32° C. for four days. The culture medium was centrifuged (2000 rpm) to separate a culture supernatant and a fungus body. The fungus body was dissolved in PBS, fragmented with ultrasonic waves, and centrifuged (2000 rpm), and the supernatant was recovered to prepare a fungus body extract through a 0.22-μm filter. The *Malassezia* fungus body extract, the medium only, the *Malassezia* culture supernatant, the MGL_1304 protein (rMGL) prepared in Example 3, and QRX are electrophoresed and immunoblotted with each atopic dermatitis patient serum from two patients (in FIGS. 8 and 9, the atopic dermatitis patient serums used are different).

Figure 10:
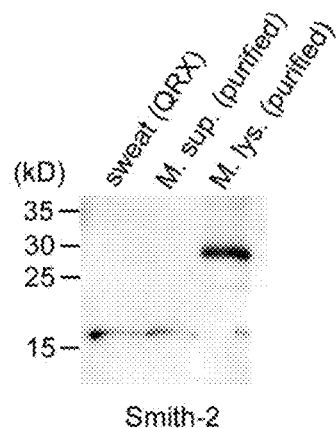
FIG. 10 shows experimental results when a purified extract of Malassezia fungus body (M. lysate (purified)), Malassezia culture supernatant (M. Sup (purified)) and a partially purified sweat antigen (sweat (QRX)) were subjected to electrophoresis to perform immunoblotting using an atopic dermatitis patient serum of one patient.

After purification of the *Malassezia* fungus body extract and the *Malassezia* culture supernatant, the purified *Malassezia* fungus body extract, the purified *Malassezia* culture supernatant, and QRX were electrophoresed and immunoblotted with the Smith2 antibody (FIG. 10). The *Malassezia* fungus body extract and the *Malassezia* culture supernatant were purified as follows. *M. Globosa* was cultured in a 2693 mDixon medium at 32° C. for four days. The culture medium was centrifuged (2000 rpm) and the supernatant was recovered to prepare the *Malassezia* culture supernatant through a 0.22-μm filter. The culture supernatant was fractionated by the ion-exchange column chromatography and the reverse-phase column chromatography described in Example 1 using the histamine release as an index, so as to recover a fraction having the histamine release activity.

Figure 8:
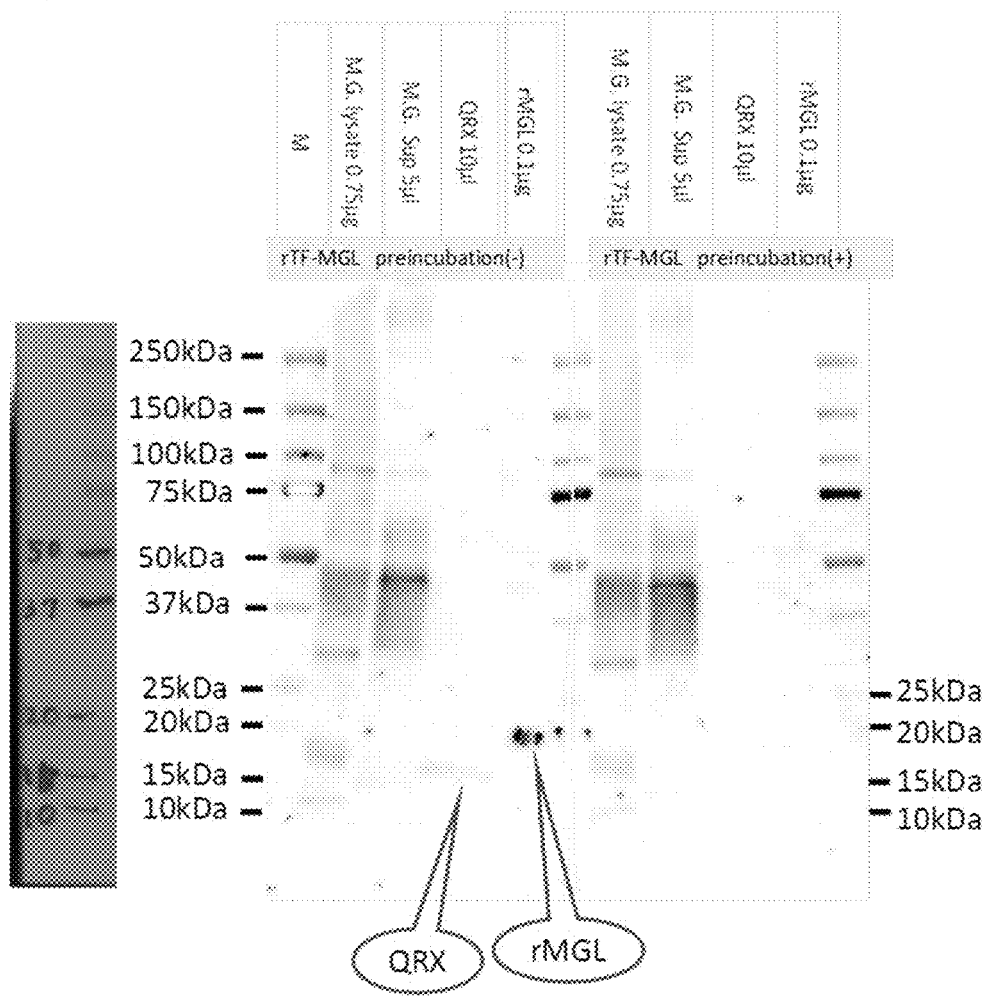
FIG. 8 shows experimental results when an extract of Malassezia fungus body (M.G. lysate), Malassezia culture supernatant (M.G. Sup), MGL_1304 recombinant protein (rMGL) and a partially purified sweat antigen (QRX) were subjected to electrophoresis to perform immunoblotting using atopic dermatitis patient serum of one patient. In particular.
Figure 9:
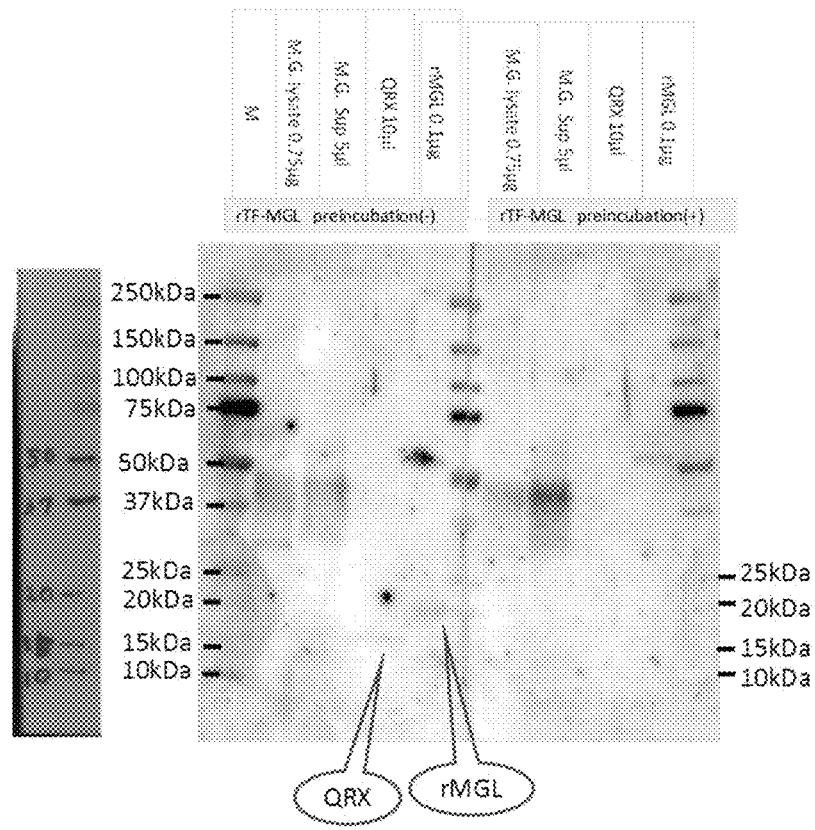
FIG. 9 shows experimental results when an extract of Malassezia fungus body (M.G. lysate), Malassezia culture supernatant (M.G. Sup), MGL_1304 recombinant protein (rMGL) and partially purified sweat antigen (QRX) were subjected to electrophoresis to perform the immunoblotting as performed in FIG. 8 except for using an atopic dermatitis patient serum of one person different from the patient of the serum used in FIG. 8.

Although rMGL exhibited a molecular weight (about 23 kDa) expected from the DNA sequence (FIG. 2), a protein detected in the atopic dermatitis patient serum, which is present in the lysate of the *Malassezia* fungus body, exhibited about 30 k Da, indicating that MGL is subjected to post-translational modification (FIGS. 8, 9, and 10). On the other hand, a protein detected in the atopic dermatitis patient serum, which is present in the culture supernatant of the *Malassezia* fungus body, exhibited about 17 kDa, which is the same as QRX (FIG. 10). Therefore, it was revealed that MGL is further modified when it is secreted from the fungus body. A band of about 30 kDa present in the lysate of the *Malassezia* fungus body, a band of about 17 kDa present in the culture serum of the *Malassezia* fungus body, and a band of QRX disappeared when the atopic dermatitis patient serum was pretreated with rMGL (FIGS. 8 and 9). In terms of the histamine release activity, the purified antigen from the culture supernatant secreted from the *Malassezia* fungus body shows higher activity compared to rMGL (full-length rMGL obtained by an enzyme treatment to cleave TF bound to rMGL for the protein expression).

Example 8

Binding of Antibody Raised Against Recombinant MGL_1304 Protein as Immunogen to QRX and Recombinant MGL_1304 Protein The recombinant MGL_1304 protein (rMGL_1304) prepared in Example 3 was used for immunization of Balb/c mice, and screening was performed by using the binding property to rMGL as an index so as to prepare a monoclonal antibody producing strain (MGLab). The binding properties of these antibodies to the polypeptides (P1 to 4) prepared in Example 5 having the sequences obtained by fragmenting the MGL_1304 protein into four pieces were examined by ELISA.

P1 to P4 fused with TF (TF-P1 to 4) dissolved in PBS resulting in 3 μg/ml solution were coated on a 96-well microplate (50 μl/well) and blocked by BSA, and the monoclonal antibodies were added to detect mouse IgG binding to the polypeptides using enzyme-labeled anti-mouse IgG antibodies.

Figure 12:
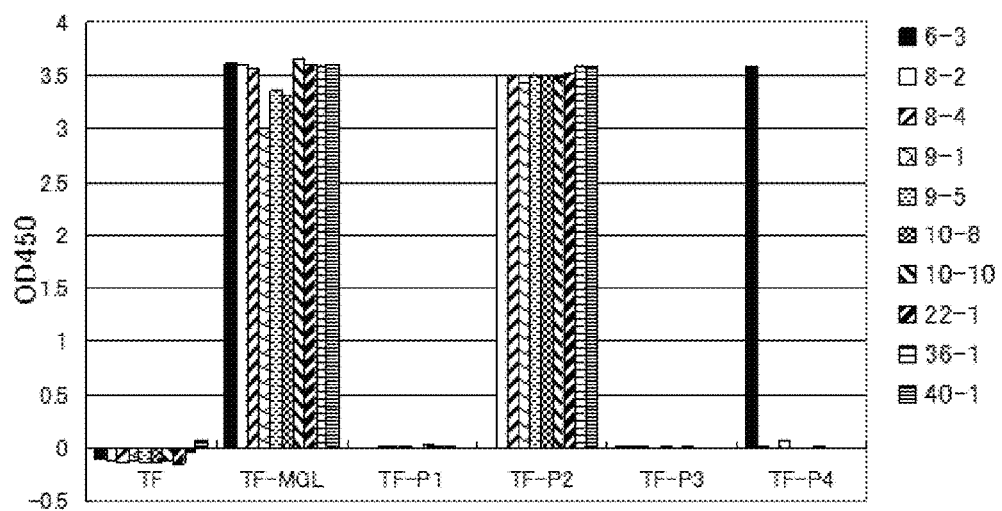
FIG. 12 shows sites of MGL_1304 protein recognized by monoclonal antibodies MGLab6-3, MGLab8-2, MGLab8-4, MGLab9-1, MGLab9-5, MGLab10-8, MGLab10-10, MGLab22-1, MGLab36-1 and MGLab40-1 created by immunizing mice with a recombinant MGL_1304 protein. ELISA was performed for testing whether the antibodies recognize Trigger Factor (TF), a TF-fused MGL_1304 protein (TF-MGL), a peptide (TF-P1) corresponding to an amino acid sequence 1-50 of the TF-fused MGL_1304 protein, a peptide (TF-P2) corresponding to an amino acid sequence 46-100 of the TF-fused MGL_1304 protein, a peptide (TF-P3) corresponding to an amino acid sequence 96-140 of the TF-fused MGL_1304 protein, and a peptide (TF-P4) corresponding to an amino acid sequence 136-183 of the TF-fused MGL_1304 protein. The results indicated that the monoclonal antibodies created by immunizing mice with the recombinant MGL_1304 protein recognize the amino acid sequence 46-100 of the MGL_1304 protein except that MGLab6-3 recognizes the amino acid sequence 136-183 of the MGL_1304 protein.

As a result, MGLab6-3 bound to P4 while MGLab8-2, 8-4, 9-1, 9-5, 10-8, 10-10, 22-1, 36-1, and 40-1 bound to P2, indicating preparation of monoclonal antibodies which recognize epitopes different from Smith-2 described in Example 3 (FIG. 12).

The results indicated that the P2 (the polypeptide corresponding to the amino acid sequence 46-100 (Seq ID NO: 11) of the MGL_1304 protein) and P4 (P4: the polypeptide corresponding to the amino acid sequence 136-183 (Seq ID NO: 13) of the MGL_1304 protein) regions may be recognition sites of an anti-MGL_1304 protein antibody in the MGL_1304 protein.

Example 9

Measurement of Anti-Sweat Antigen-Specific IgE Antibody in Patient Serum

Monoclonal antibodies MGLab8-2 (8-2) and MGLab6-3 (6-3) prepared by immunizing mice with rMGL prepared in Example 3 were used for studying whether IgE antibodies in serums of atopic dermatitis patients (AD1 and AD2) can be detected.

A 96-well ELISA plate was coated with the antibodies at 10 μg/ml and 50 μl/well and was left overnight at 4° C. The plate was washed twice, blocked by 2% BSA (one hour), and then washed twice. After 100-fold diluted QRX or 3 μg/ml of TF-MGL prepared in Example 3 was added at 100 μl/well, left for 90 minutes, and washed three times, the serum was added at 100 μl/well and left for 90 minutes. After the plate was washed three times, a solution containing HRP-labeled anti-human IgE antibody is added at 100 μl/well, left for one hour, and washed three times, and a color was developed by using TMB to measure absorbance (450 nm).

Figure 13:
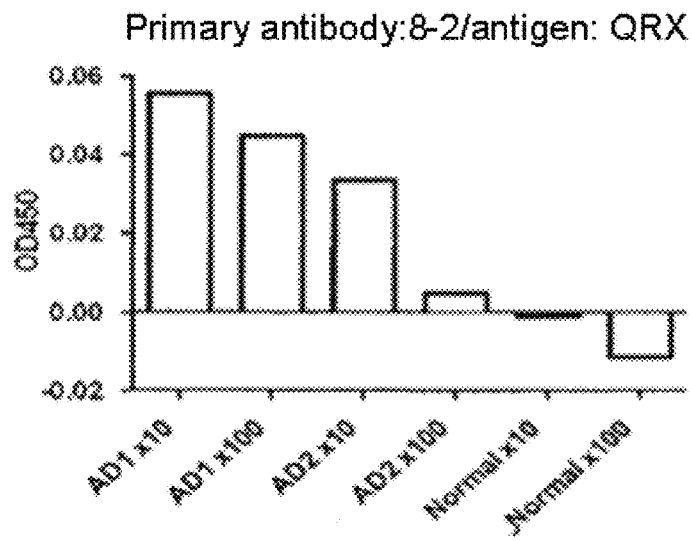
FIG. 13 shows detection of a sweat antigen-specific IgE antibody in serums of atopic dermatitis patients (AD1 and AD2) and a healthy volunteer (Nor1). An ELISA plate was coated with a mouse monoclonal antibody 8-2 prepared by immunization with the MGL_1304 recombinant protein as a primary antibody and QRX was allowed to bind thereto. The IgE antibody binding to a complex of the mouse monoclonal antibody 8-2 and QRX was detected from the serums.
Figure 14:
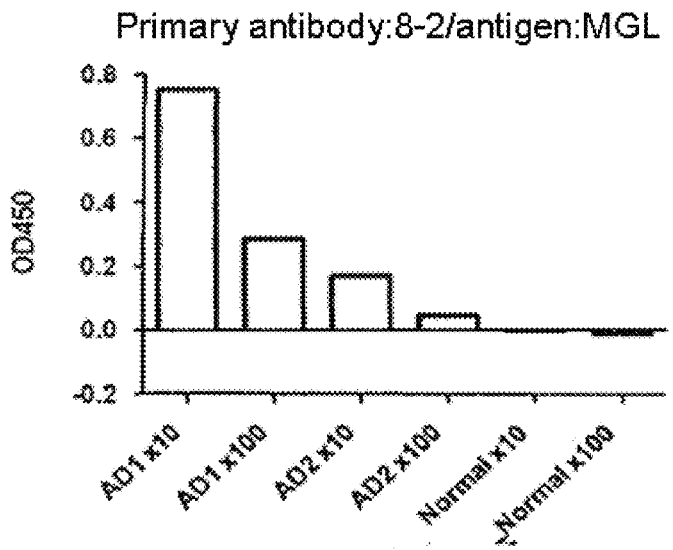
FIG. 14 shows detection of the sweat antigen-specific IgE antibody in the serums of the atopic dermatitis patients (AD1 and AD2) and the healthy volunteer (Nor1). An ELISA plate was coated with the mouse monoclonal antibody 8-2 prepared by immunization with the MGL_1304 recombinant protein as the primary antibody and rMGL was allowed to bind thereto. The IgE antibody binding to a complex of the mouse monoclonal antibody 8-2 and rMGL was detected from the serums.
Figure 15:
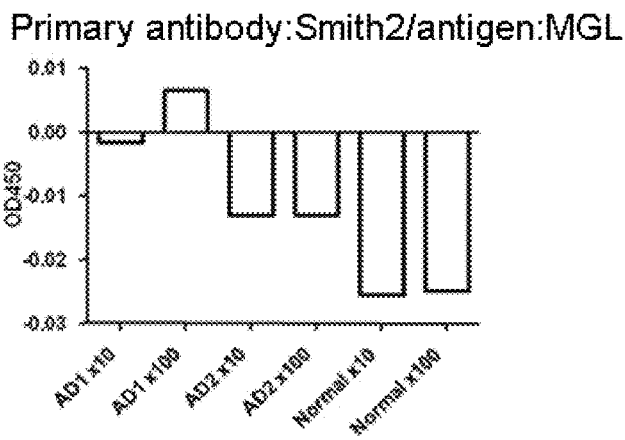
FIG. 15 shows detection of the sweat antigen-specific IgE antibody in the serums of the atopic dermatitis patients (AD1 and AD2) and the healthy volunteer (Nor1). An ELISA plate was coated with the Smith2 antibody used as the primary antibody and rMGL was allowed to bind thereto. The IgE antibody binding to a complex of the mouse monoclonal antibody 8-2 and rMGL was detected from the serums.

As a result, the monoclonal antibody MGLab8-2 prepared by immunizing mice with rMGL detected the IgE antibody in the serums of the atopic dermatitis patients via binding to QRX or rMGL. On the other hand, the Smith2 antibody was not able to detect the IgE antibody in the serums of the atopic dermatitis patients via rMGL (FIGS. 13 to 15).

Figure 16:
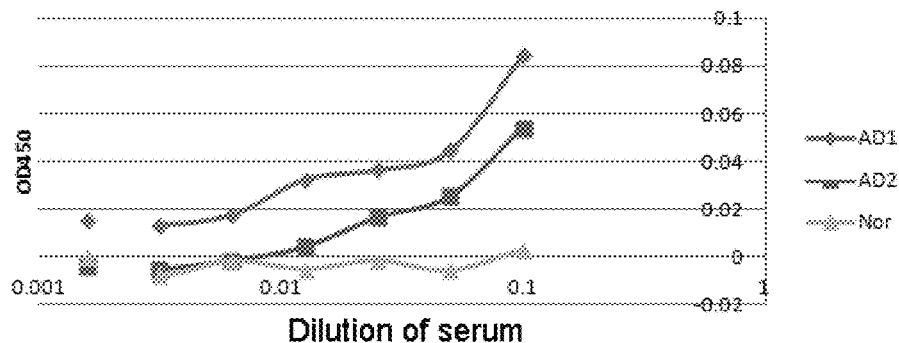
FIG. 16 shows detection of the sweat antigen-specific IgE antibody in the serums of the atopic dermatitis patients (AD1 and AD2) and the healthy volunteer (Nor1). An ELISA plate was coated with a mouse monoclonal antibody 6-3 prepared by immunization with the MGL_1304 recombinant protein as the primary antibody and rMGL was allowed to bind thereto. The IgE antibody binding to a complex of the mouse monoclonal antibody 6-3 and rMGL was detected from the serums.
Figure 17:
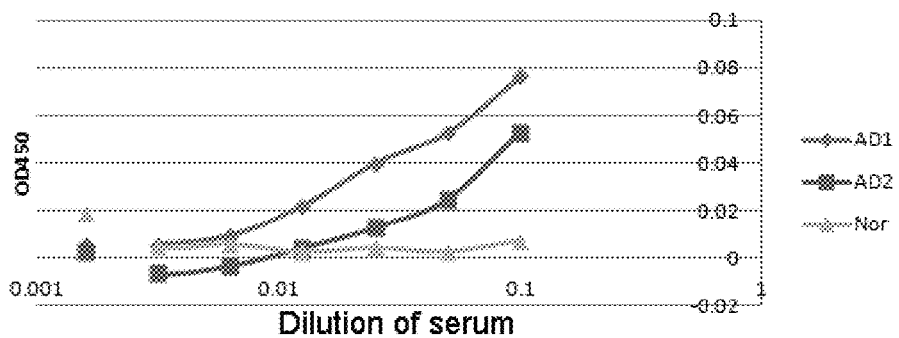
FIG. 17 shows detection of the sweat antigen-specific IgE antibody in the serums of the atopic dermatitis patients (AD1 and AD2) and the healthy volunteer (Nor1). An ELISA plate was coated with the mouse monoclonal antibody 8-2 prepared by immunization with the MGL_1304 recombinant protein as the primary antibody and rMGL was allowed to bind thereto. The IgE antibody binding to a complex of the mouse monoclonal antibody 8-2 and rMGL was detected from the serums.

Then, experiments were conducted to study whether the IgE antibody in the serum of the atopic dermatitis patient can be quantified by means of the monoclonal antibodies MGLab8-2 and MGLab6-3 prepared by immunizing mice with rMGL. As a result, the absorbance was decreased in proportion to a decrease in an IgE antibody amount due to dilution of the serum of the atopic dermatitis patient. It was revealed that the both antibodies (monoclonal antibodies MGLab8-2 and MGLab6-3) enable quantification of the IgE antibodies in the serum of the atopic dermatitis patient using rMGL (FIGS. 16 and 17).

These results indicated that a sweat allergy in atopic dermatitis can be diagnosed by utilizing the monoclonal antibody prepared by immunizing mice with rMGL.

Example 10

Measurement of Anti-Sweat Antigen-Specific IgE Antibody in Patient Serum (2)

Experiments were conducted to study whether IgE antibody specifically binding to a sweat antigen can be detected in serums of atopic dermatitis (AD), allergic rhinitis, and a healthy person (Normal) by using ELISA coating rTF-MGL prepared in Example 3.

A 96-well ELISA plate was coated with rTF or rTF-MGL at 3 μg/ml and 50 μl/well and was left overnight at 4° C. The plate was washed twice, blocked by 2% BSA (room temperature, one hour), and then washed twice. The serum diluted by 1% BSA was added at 100 μl/well and left for one hour at room temperature. After the plate was washed three times, a solution containing HRP-labeled anti-human IgE antibodies is added at 100 μl/well, left for one hour, and washed three times, and a color was developed by using TMB to measure absorbance (450 nm).

Figure 18:
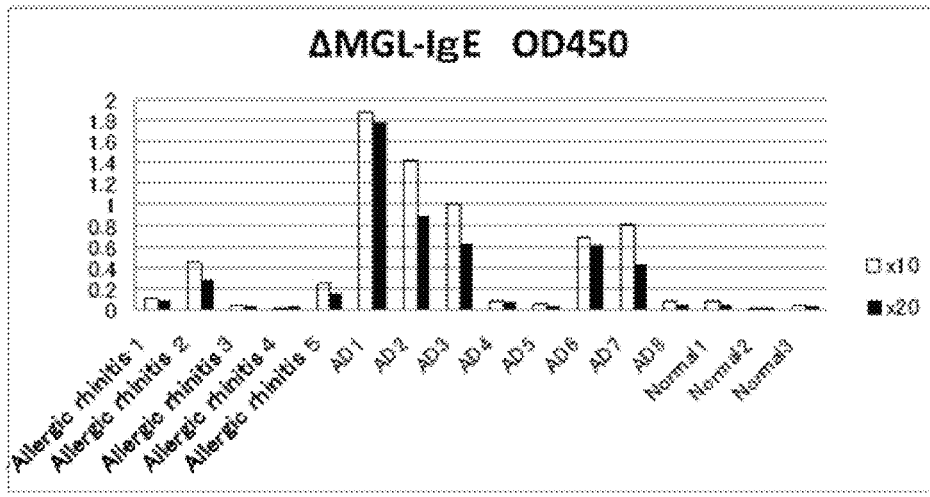
FIG. 18 shows detection of the sweat antigen-specific IgE antibody in serums of allergic rhinitis patients (allergic rhinitis 1-5), atopic dermatitis patients (AD1-8) and healthy volunteer (Nor1-3). An ELISA plate was coated with the MGL_1304 recombinant protein (rMGL) and a binding IgE antibody was detected from the serums. The serums were diluted 10 times (×10) and 20 times (×20) before being used in the test. The vertical axis indicates absorbance at 450 nm.
Figure 19:
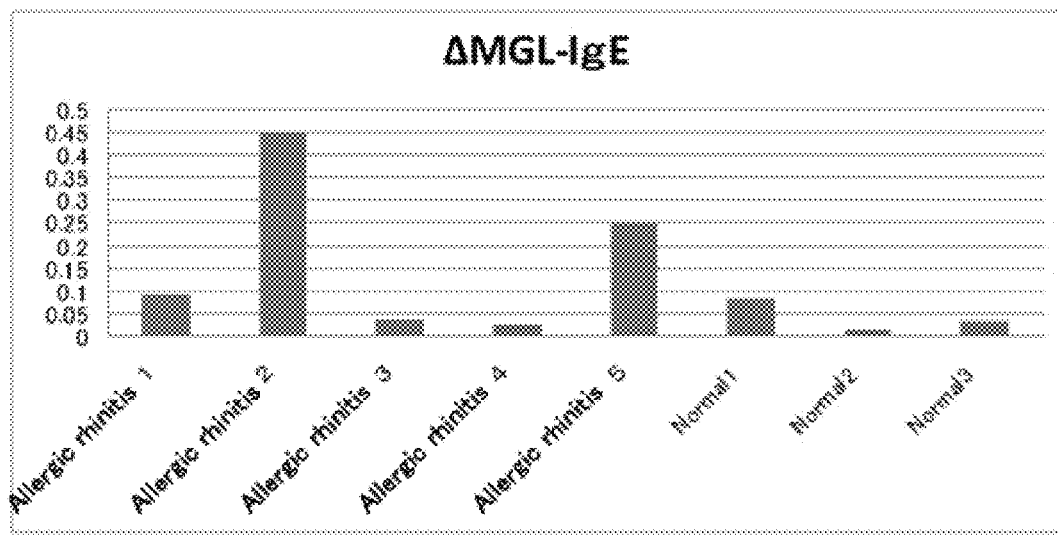
FIG. 19 shows detection of the sweat antigen-specific IgE antibody in the serums of the allergic rhinitis patients (allergic rhinitis 1-5) and the healthy volunteer (Nor1-3). An ELISA plate was coated with the MGL_1304 recombinant protein (rMGL) and a binding IgE antibody was detected from the serums. The serums were diluted 10 times (×10) before being used in the test. The vertical axis indicates absorbance at 450 nm.

As a result, IgE binding to the sweat antigen (MGL) was detected in the serums of the atopic dermatitis patients and the allergic rhinitis patients by ELISA coating rMGL (FIGS. 18 and 19). On the other hand, IgE binding to the sweat antigen (MGL) was not detected in the serum of the healthy person (FIGS. 18 and 19).

These results indicated that a sweat allergy can be diagnosed in atopic dermatitis and allergic rhinitis patients by ELISA coating rMGL.

Example 11

Measurement of Anti-MGL Antibody in Patient Subjected to Hyposensitization Therapy QRX was repeatedly subcutaneously injected to a sweat allergy patient at concentration gradually increased from a low concentration. Serums were collected over time and changes in the anti-MGL antibody amount in the collected serums were measured by ELISA using the anti-human IgE antibody, the anti-human IgG antibody, or the anti-human IgG4 antibody, where rMGL prepared in Example 3 was coated.

Figure 20:
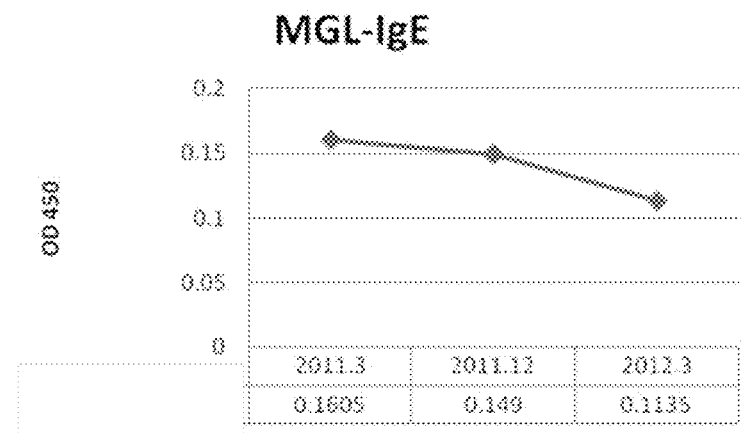
FIG. 20 shows time course of amount of antibodies binding to rMGL in serum of a patient subjected to a hyposensitization therapy by repeated subcutaneous injections of QRX. The blood of the patient was collected three times (March 2011 (2011.3), December 2011 (2011.12), and March 2012 (2012.3)) to prepare the serums, and an rMGL-coated ELISA plate was used for measuring a change in amount of anti-MGL human IgE antibodies in the serums.
Figure 21:
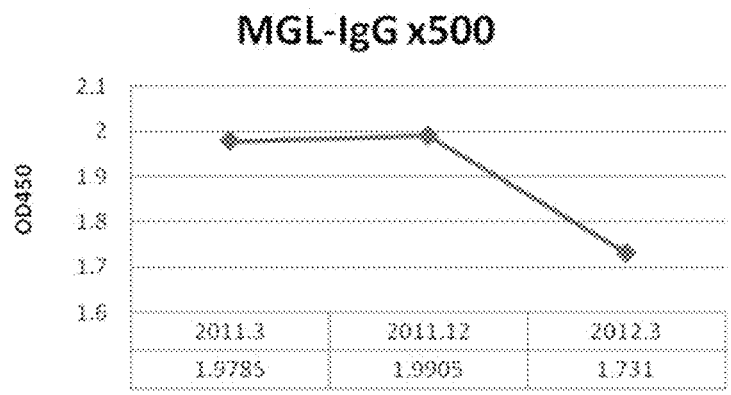
FIG. 21 shows time course of amount of antibodies binding to rMGL in serum of the patient subjected to the hyposensitization therapy by repeated subcutaneous injections of QRX. The blood of the patient was collected three times (March 2011 (2011.3), December 2011 (2011.12), and March 2012 (2012.3)) to prepare the serums, and an rMGL-coated ELISA plate was used for measuring a change in amount of anti-MGL human IgG antibodies in the serums.
Figure 22:
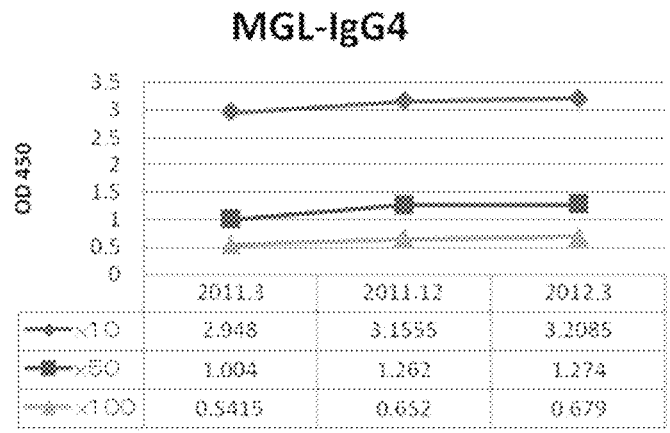
FIG. 22 shows time course of amount of antibodies binding to rMGL in serum of the patient subjected to the hyposensitization therapy by repeated subcutaneous injections of QRX. The blood of the patient was collected three times (March 2011 (2011.3), December 2011 (2011.12), and March 2012 (2012.3)) to prepare the serums, which were diluted 10 times (×10), 50 times (×50), and 100 times (×100), and an rMGL-coated ELISA plate was used for measuring a change in amount of anti-MGL human IgG4 antibodies.

As a result, changes in respective antibody amounts of the anti-MGL-IgE antibody, the anti-MGL-IgG antibody, and the anti-MGL-IgG4 antibody were measured in patient serums (FIGS. 20 to 22). Although the concentrations of the anti-MGL-IgE and the anti-MGL-IgG (including sub-types 1 to 4) was decreased in the course of treatment, the anti-MGL-IgG4 was increased in the course of treatment. This phenomenon is consistent with a general knowledge that IgE is slightly decreased while the concentration of IgG4 against the antigen thereof at first rises in the hyposensitization therapy.

According to a clinical diagnosis by a physician, DLQI, which is an index indicative of quality of life, was improved by due to the hyposensitization therapy applied to the patient.

These results indicated that rMGL is useful as an antigen for the hyposensitization therapy as is the case with QRX, and also indicated that rMGL is useful for determination of a therapeutic effect of the hyposensitization therapy.

Example 12

Study on Production Amount of MGL_1304 Protein in Culturing Using Buffer Solution of *M. globosa*

Figure 23:
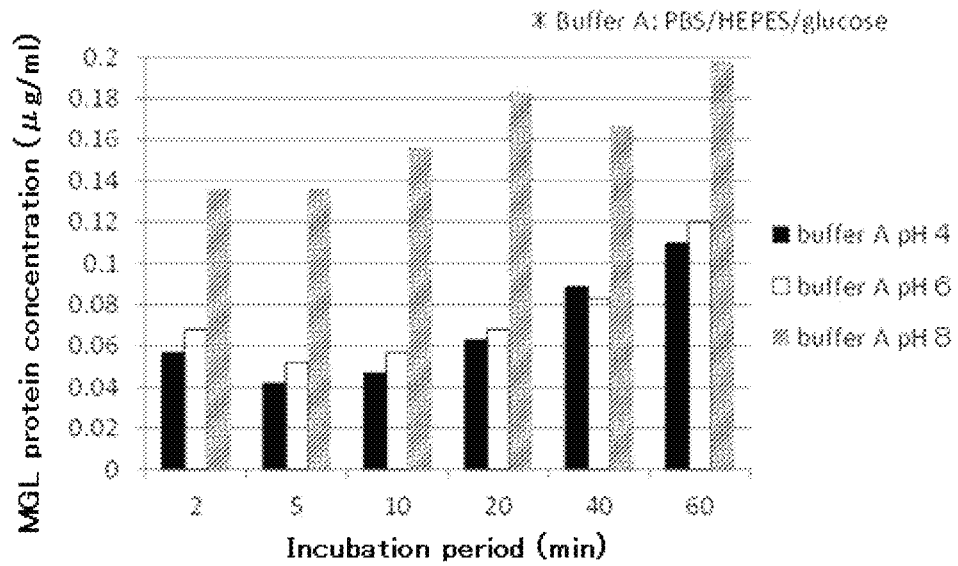
FIG. 23 shows concentration of the MGL_1304 protein (protein coded by the MGL_1304 gene) produced in culture supernatant when *Malassezia globosa* was cultured in buffer A (PBS/HEPES/glucose) at pH 4, pH 6, or pH 8 for 2 to 60 minutes.

*M. Globosa* was cultured in a 2693 mDixon medium at 32° C. for four days. The culture supernatant was removed and the fungus body was washed with a buffer solution (buffer A: PBS/HEPES/glucose buffer solution) at pH 4, pH 6, or pH 8. The buffer solutions were subsequently used in culturing for 2 to 60 minutes and a concentration of the produced MGL_1304 protein was measured by ELISA. As a result, the production of the MGL_1304 protein was increased when the culture was performed using the buffer solution at pH 8 (FIG. 23).

The invention claimed is:

1. A method of detecting antibody binding to a sweat allergy antigen protein, comprising
contacting a biological sample from a human with a sweat allergy antigen protein selected from the group consisting of
(i) a protein comprising an amino acid sequence having 90% or more sequence identity to the amino acid sequence of SEQ ID NO: 1; and
(ii) a peptide comprising an amino acid sequence having 90% or more sequence identity to the amino acid sequence of any of SEQ ID NO: 2 to 7; and
detecting the antibody binding to the sweat allergy antigen protein.

2. The method of claim 1, further comprising measuring an amount of the antibody binding to a sweat allergy antigen protein.

3. The method of claim 1, further comprising determining an amount of the antibody binding to a sweat allergy antigen protein in the sample based on results from detecting the antibody that binds to the protein or peptide, wherein the contacting the sample with the sweat allergy antigen protein is performed using the sweat allergy antigen protein at a plurality of known concentrations.

4. The method of claim 1, wherein the sweat allergy antigen protein is a protein comprising the amino acid sequence of SEQ ID NO: 1.

5. The method of claim 1, wherein the sweat allergy antigen protein is a protein consisting of the amino acid sequence of SEQ ID NO: 1.

6. The method of claim 1, wherein the sweat allergy antigen protein is a peptide comprising the amino acid sequence of any of SEQ ID NO: 2 to 7.

7. The method of claim 1, wherein the sweat allergy antigen protein is a peptide consisting of the amino acid sequence of any of SEQ ID NO: 2 to 7.

8. The method of claim 1, wherein the biological sample from a human includes sweat, skin washings, a solution of an extract of skin, a serum, or a plasma.

9. The method of claim 1, wherein the detecting the antibody is performed using Western blotting or enzyme-linked immunosorbent assay (ELISA).

10. The method of claim 1, wherein the sweat allergy antigen protein is a protein secreted from a fungus body of *Malassezia globosa*, has a molecular weight of about 17 kDa, and binds to (i) serum derived from a sweat allergy patient and/or (ii) smith2 antibody.

11. The method of claim 1, wherein the sweat allergy antigen protein is a protein present in a fungus body of *Malassezia globosa*, has a molecular weight of about 30 kDa, and binds to (i) serum derived from a sweat allergy patient and/or (ii) smith2 antibody.

12. A method of diagnosing a sweat allergy or a disease relating to a sweat allergy antigen protein, comprising
    detecting antibody binding to a sweat allergy antigen protein in a sample from a human according to the method of claim 1.

* * * * *